(12) United States Patent
Frank et al.

(10) Patent No.: US 9,233,950 B2
(45) Date of Patent: Jan. 12, 2016

(54) CO-CRYSTALS AND SALTS OF CCR3-INHIBITORS

(71) Applicant: Boehringer Ingelheim International GmbH, Ingelheim am Rhein (DE)

(72) Inventors: Markus Frank, Ulm (DE); Hans Haeberle, Maselheim (DE); Manuel Henry, Biberach an der Riss (DE); Thorsten Pachur, Biberach an der Riss (DE); Marco Santagostino, Mittelbiberach (DE); Uwe Stertz, Biberach an der Riss (DE); Thomas Trebing, Biberach an der Riss (DE); Ulrike Werthmann, Biberach an der Riss (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/572,889

(22) Filed: Dec. 17, 2014

(65) Prior Publication Data

US 2015/0105371 A1  Apr. 16, 2015

Related U.S. Application Data

(63) Continuation of application No. 14/160,646, filed on Jan. 22, 2014, now abandoned, which is a continuation of application No. 13/267,417, filed on Oct. 6, 2011, now Pat. No. 8,742,115.

(30) Foreign Application Priority Data

Oct. 7, 2010   (EP) ..................................... 10186901

(51) Int. Cl.
| | |
|---|---|
| C07D 211/68 | (2006.01) |
| C07D 401/14 | (2006.01) |
| C07D 211/58 | (2006.01) |
| C07D 213/81 | (2006.01) |
| C07D 401/04 | (2006.01) |

(52) U.S. Cl.
CPC ............ *C07D 401/14* (2013.01); *C07D 211/58* (2013.01); *C07D 213/81* (2013.01); *C07D 401/04* (2013.01)

(58) Field of Classification Search
None
See application file for complete search history.

(56) References Cited

U.S. PATENT DOCUMENTS

| | | | |
|---|---|---|---|
| 4,289,781 A | 9/1981 | Bengtsson et al. |
| 6,433,165 B1 | 8/2002 | Luly et al. |
| 6,476,054 B1 | 11/2002 | Caldwell et al. |
| 6,936,718 B2 | 8/2005 | Chen et al. |
| 7,176,219 B2 | 2/2007 | Hayakawa et al. |
| 7,632,829 B2 | 12/2009 | Aebi et al. |
| 8,278,302 B2 | 10/2012 | Grundl et al. |
| 2005/0090504 A1 | 4/2005 | Gong et al. |
| 2005/0182095 A1 | 8/2005 | Ting et al. |
| 2009/0123375 A1 | 5/2009 | Ambati |
| 2010/0261687 A1 | 10/2010 | Grundl et al. |
| 2012/0264729 A1 | 10/2012 | Frank et al. |
| 2013/0023517 A1 | 1/2013 | Grundl et al. |
| 2013/0261153 A1 | 10/2013 | Nivens et al. |
| 2013/0261307 A1 | 10/2013 | Duran et al. |
| 2013/0266646 A1 | 10/2013 | Fetscher et al. |
| 2014/0135307 A1 | 5/2014 | Frank et al. |
| 2015/0099783 A1 | 4/2015 | Nivens et al. |

FOREIGN PATENT DOCUMENTS

| | | |
|---|---|---|
| EP | 0468187 A2 | 1/1992 |
| JP | 2002501052 A | 1/2002 |
| JP | 2002501898 A | 1/2002 |
| JP | 2005518424 A | 6/2005 |
| JP | 2006137718 A | 6/2006 |
| JP | 2006518713 A | 8/2006 |
| JP | 2008503495 A | 2/2008 |
| JP | 2009534346 A | 9/2009 |
| WO | 2004064762 A2 | 8/2004 |
| WO | 2006007448 A2 | 1/2006 |
| WO | 2006083390 A2 | 8/2006 |
| WO | 2006091671 A1 | 8/2006 |
| WO | 2006095671 A1 | 9/2006 |

(Continued)

OTHER PUBLICATIONS

Abstract in English of JP2006137718, 2006.
Bachert, C. et al., "Pharmacological Management of Nasal Polyposis." Drugs, 2005, vol. 65, No. 11, pp. 1537-1552.
Blanchard, C. et al., "Eotaxin-3 and a Uniquely Conserved Gene-Expression Profile in Eosinophilic Esophagitis." The Journal of Clinical Investigation, 2006, vol. 116, No. 2, pp. 536-547.
De Lucca et al., "Discovery and Structure-Activity Relationship of N-(Ureidoalkyl)-Benzyl-Piperidines as Potent Small Molecule CC Chemokine Receptor-3 (CCR3) Antagonists". Journal of Medicinal Chemistry, vol. 45, 2002, pp. 3794-3804.
International Search Report and Written Opinion for PCT/EP2011/067437 mailed Jan. 23, 2012.
Kozma, David "Resolving Agents"., CRC Handbook of Optical Resolutions Via Diastereomeric Salt Formation, Chapter 4, CRC Press LLC, Boca Raton, 2001, 47 pages.
London et al., "Update and Review of Central Retinal Vein Occlusion". Current Opinion in Ophthalmology, vol. 22, 2011, pp. 159-165.

(Continued)

*Primary Examiner* — Heidi Reese
(74) *Attorney, Agent, or Firm* — Michael P. Morris; Edward S. Lazer

(57) ABSTRACT

This invention relates to co-crystals and salts of CCR3 inhibitors of formula 1,

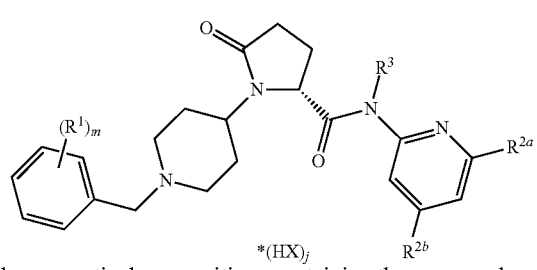

pharmaceutical compositions containing the same, and methods of using the same as agents for treatment and/or prevention of diseases related with the CCR3-receptor.

4 Claims, No Drawings

(56) References Cited

FOREIGN PATENT DOCUMENTS

| WO | 2007116313 | A2 | 10/2007 |
|---|---|---|---|
| WO | 2008092681 | A1 | 8/2008 |
| WO | 2009145721 | A1 | 12/2009 |
| WO | 2010115836 | A1 | 10/2010 |
| WO | 2012045803 | A1 | 4/2012 |
| WO | 2013149986 | A1 | 10/2013 |
| WO | 2013149987 | A1 | 10/2013 |

OTHER PUBLICATIONS

Sato et al., "Synthesis and structure-activity relations of N-{1-[(6-fluoro-2-naphthyl)methyl]piperidin-4-yl}benzamide derivatives as novel CCR3 antagonists". Bioorganic & Medicinal Chemistry, vol. 16, 2008, pp. 144-156.

Takeda, A. et al., "CCR3 is a Target for Age-Related Macular Degeneration Diagnosis and Therapy." Nature, 2009, vol. 460, No. 7252, pp. 225-230.

Ting et al., "The synthesis of substituted bipiperidine amide compounds as CCR3 antagonists". Bioorganic & Medicinal Chemistry Letters, No. 15, 2005, pp. 1375-1378.

Wuts et al., "Protection for the Carboxyl Group". Greene's Protective Groups in Organic Synthesis, Ch. 5, 4th Edition, NY Wiley, 2007, pp. 553-559 and pp. 582-588.

US 9,233,950 B2

CO-CRYSTALS AND SALTS OF CCR3-INHIBITORS

FIELD OF THE INVENTION

This invention relates to co-crystals and salts of CCR3 inhibitors, pharmaceutical compositions containing one of those, and methods of using the same as agents for treatment and/or prevention of a wide variety of inflammatory, infectious, and immunoregulatory disorders and diseases, including asthma and allergic diseases, chronic obstructive pulmonary disease, infection by pathogenic microbes (including viruses), autoimmune pathologies such as the rheumatoid arthritis and atherosclerosis as well as age-related macular degeneration (AMD), diabetic retinopathy and diabetic macular edema.

BACKGROUND INFORMATION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998); Rollins, Blood, 90, 909-928 (1997); Lloyd, Curr Opin Pharmacol., 3, 443-448 (2003); Murray, Current Drug Targets., 7, 579-588 (2006); Smit, Eur J. Pharmacol., 533, 277-88 (2006)

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-Ia, MIP-1, the monocyte chemotactic proteins (MCP-1, MCP-2, MCP-3, MCP-4, and MCP-5) and the eotaxins (−1, −2, and −3) are chemotactic for, among other cell types, macrophages, T lymphocytes, eosinophils, mast cells, dendritic cells, and basophils. Also in existence are the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seventransmembrane-domain proteins (reviewed in Horuk, Trends Pharm. Sci., 15, 159-165 (1994); Murphy, Pharmacol Rev., 54 (2):227-229 (2002); Allen, Annu. Rev. Immunol., 25, 787-820 (2007)) which are termed "chemokine receptors." On binding their cognate ligands, chemokine receptors transduce an intracellular signal through the associated trimeric G proteins, resulting in, among other responses, a rapid increase in intracellular calcium concentration, activation of G-proteins, changes in cell shape, increased expression of cellular adhesion molecules, degranulation, promotion of cell migration, survival and proliferation. There are at least eleven human chemokine receptors that bind or respond to CC chemokines with the following characteristic patterns: CCR-1 (or "CKR-1" or "CC-CKR-1") [MIP-Ia, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR3 (or "CKR-3" or "CC-CKR-3") [eotaxin-1, eotaxin-2, RANTES, MCP-3, MCP-4](Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-Ia, RANTES, MCP-1] (Power et al., J. Biol. Chem., 270, 19495-19500 (1995), Luster, New Eng. J. Med., 338, 436-445 (1998)); CCR-5 (or "CKR-5" OR "CCCKR-5") [MIP-Ia, RANTES, MIP-Ip] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1p] (Napolitano et al., J. Immunol., 157, 2759-2763 (1996), Bernardini et al., Eur. J. Immunol., 28, 582-588 (1998)); CCR-10 (or "CKR-10" or "CC-CKR-10") [MCP-1, MCP-3] (Bonini et al, DNA and Cell Biol., 16, 1249-1256 (1997)); and CCR31 (or "CKR-11" or "CC-CKR-11") [MCP-1, MCP-2, MCP-4] (Schweickart et al., J Biol Chem, 275 9550-9556 (2000)).

In addition to the mammalian chemokine receptors, the Decoy receptors CCX-CKR, D6 and DARC/Duffy as well proteins expressed by mammalian cytomegaloviruses, herpes viruses and poxviruses, exhibit binding properties of chemokine receptors (reviewed by Wells and Schwartz, Curr. Opin. Biotech., 8, 741-748 (1997); Comerford, Bioessays., 29(3):237-47 (2007)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR-4, CCR2, CCR3, CCR5 and CCR8, can act as co receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis, Grave's disease, chronic obstructive pulmonary disease, and atherosclerosis. For example, the chemokine receptor CCR3 is expressed among others on eosinophils, basophils, TH2 cells, alveolar macrophages, mast cells, epithelial cells, microglia cells, astrocytes and fibroblasts. CCR3 plays a pivotal role in attracting eosinophils to sites of allergic inflammation and in subsequently activating these cells. The chemokine ligands for CCR3 induce a rapid increase in intracellular calcium concentration, increased GTP exchange of G-proteins, increased ERK phosphorylation, enhanced receptor internalization, eosinophil shape change, increased expression of cellular adhesion molecules, cellular degranulation, and the promotion of migration. Accordingly, agents that inhibit chemokine receptors would be useful in such disorders and diseases. In addition, agents that inhibit chemokine receptors would also be useful in infectious diseases such as by blocking infection of CCR3 expressing cells by HIV or in preventing the manipulation of immune cellular responses by viruses such as cytomegaloviruses.

Therefore, CCR3 is an important target and antagonism of CCR3 is likely to be effective in the treatment of inflammatory, eosinophilic, immunoregulatory and infectious disorders and diseases (Wegmann, Am J Respir Cell Mol. Biol., 36(1):61-67 (2007); Fryer J Clin Invest., 116(1):228-236 (2006); De Lucca, Curr Opin Drug Discov Devel., 9(4):516-524 (2006)

So, the problem underlying the present invention was the provision of CCR3 antagonists, preferred with reduced side effects which are not only potent CCR3-inhibitors, but also are useful for manufacturing a medicament for the prevention and/or treatment of diseases wherein the activity of a CCR3-receptor is involved.

It has been found surprisingly that the substituted piperidines of formula 1 are highly suitable as CCR3 antagonists, having less side effects, e.g. inhibition of norepinephrine (NET), dopamine (DAT) or serotonin reuptake transporters (5-HTT) as described by Watson P S, Bioorg Med Chem. Lett., 16(21):5695-5699 (2006), or inhibition of 5HT2A, 5HT2C or Dopamine D2 receptors as described by De Lucca, J Med. Chem., 48(6):2194-2211 (2005), or inhibition of the hERG channel as described by De Lucca, Curr Opin Drug Discov Devel., 9(4):516-524 (2006), or inhibition of the alpha1B adrenergic receptor.

Nevertheless such compounds are bases and thus could be problematic for the manufacturing of a medicament since their physical behavior can cause problems finding a suitable pharmaceutical form. This could be structural problems like stability, light sensitiveness or deliquescence, but also physical problem e.g. if a compound is not soluble or not suitable for common manufacturing processes like milling.

Now, it has been surprisingly found that the claimed co-crystals or salts of the compounds of formula 1 are fulfilling enough criteria for a pharmaceutical development to manufacture a medicament as above described e.g. a sufficient stability, a controllable deliquescence, a solubility high enough to be useful as a medicament, a solid state useful for standard manufacturing processes or a sufficiently defined crystal form.

DESCRIPTION OF THE INVENTION

Subject matter of the instant invention is co-crystals of compounds of formula 1

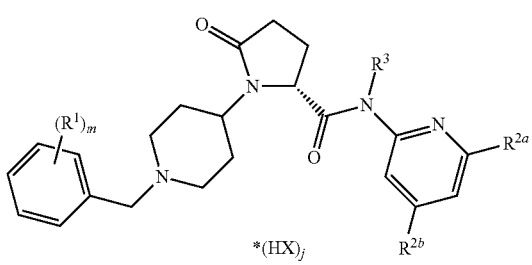

wherein
$R^1$ is $C_{1-6}$-alkyl, $C_{1-6}$-haloalkyl, O—$C_{1-6}$-haloalkyl, halogene;
m is 1, 2 or 3; preferably 1 or 2;
$R^{2a}$ and $R^{2b}$ are each independently selected from H, $C_{1-6}$-alkyl, $C_{1-6}$-alkenyl, $C_{1-6}$-alkynyl, $C_{3-6}$-cycloalkyl, COO—$C_{1-6}$-alkyl, O—$C_{1-6}$-alkyl, CONR$^{2b.1}$R$^{2b.2}$, halogene;
$R^{2b.1}$ is H, $C_{1-6}$-alkyl, $C_{0-4}$-alkyl-$C_{3-6}$-cycloalkyl, $C_{1-6}$-haloalkyl;
$R^{2b.2}$ is H, $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
$R^3$ is H, $C_{1-6}$-alkyl;
X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate; preferably chloride or dibenzoyltartrate j is 0, 0.5, 1, 1.5 or 2; preferably 1 or 2;
with a co-crystal former selected from the group consisting of orotic acid, hippuric acid, L-pyroglutamic acid, D-pyroglutamic acid, nicotinic acid, L-(+)-ascorbic acid, saccharin, piperazine, 3-hydroxy-2-naphtoic acid, mucic (galactaric) acid, pamoic (embonic) acid, stearic acid, cholic acid, deoxycholic acid, nicotinamide, isonicotinamide, succinamide, uracil, L-lysine, L-proline, D-valine, L-arginine, glycine, preferably ascorbic acid, mucic acid, pamoic acid, succinamide, nicotinic acid, nicotinamide, isonicotinamide, l-lysine, l-proline, Those co-crystals are useful for manufacturing a medicament for the prevention and/or treatment of diseases wherein the activity of a CCR3-receptor is involved.

Another aspect of the invention are co-crystals of compounds of formula 1, wherein
$R^{2a}$ is H, $C_{1-6}$-alkyl, $C_{1-6}$-alkenyl, $C_{1-6}$-alkynyl, $C_{3-6}$-cycloalkyl, O—$C_{1-6}$-alkyl, CONR$^{2a.1}$R$^{2a.2}$;
$R^{2a.1}$ is H, $C_{1-6}$-alkyl, $C_{1-6}$-haloalkyl;
$R^{2a.2}$ is H, $C_{1-6}$-alkyl;
$R^{2b}$ is H, $C_{1-6}$-alkyl, $C_{1-6}$-alkenyl, $C_{1-6}$-alkynyl, $C_{3-6}$-cycloalkyl, COO—$C_{1-6}$-alkyl, O—$C_{1-6}$-alkyl, CONR$^{2b.1}$R$^{2b.2}$, halogene;
$R^{2b.1}$ is H, $C_{1-6}$-alkyl, $C_{0-4}$-alkyl-$C_{3-6}$-cycloalkyl, $C_{1-6}$-haloalkyl;
$R^{2b.2}$ is H, $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
and the remaining residues are defined as above.

Another aspect of the invention are co-crystals of compounds of formula 1, wherein
$R^{2a}$ is H, $C_{1-6}$-alkyl, $C_{1-6}$-alkynyl, $C_{3-6}$-cycloalkyl, O—$C_{1-6}$-alkyl, CONR$^{2a.1}$R$^{2a.2}$;
$R^{2a.1}$ is $C_{1-6}$-alkyl;
$R^{2a.2}$ is H;
$R^{2b}$ is H, $C_{1-6}$-alkyl, O—$C_{1-6}$-alkyl, CONR$^{2b.1}$R$^{2b.2}$;
$R^{2b.1}$ is $C_{1-6}$-alkyl, $C_{0-4}$-alkyl-$C_{3-6}$-cycloalkyl, $C_{1-6}$-haloalkyl;
$R^{2b.2}$ is H, $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
and the remaining residues are defined as above.

Another aspect of the invention are co-crystals of compounds of formula 1, wherein
$R^{2a}$ is H, $C_{1-4}$-alkyl, $C_{1-4}$-alkynyl, $C_{3-6}$-cycloalkyl, O—$C_{1-4}$-alkyl, CONR$^{2a.1}$R$^{2a.2}$;
$R^{2a.1}$ is $C_{1-4}$-alkyl;
$R^{2a.2}$ is H;
$R^{2b}$ is H, $C_{1-4}$-alkyl, O—$C_{1-4}$-alkyl, CONR$^{2b.1}$R$^{2b.2}$;
$R^{2b.1}$ is $C_{1-4}$-alkyl, $C_{0-4}$-alkyl-$C_{3-6}$-cycloalkyl, $C_{1-4}$-haloalkyl;
$R^{2b.2}$ is H, $C_{1-4}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
and the remaining residues are defined as above.

Another aspect of the invention are co-crystals of compounds of formula 1, wherein
$R^{2a}$ is H, $C_{1-4}$-alkyl,
$R^{2b}$ is H, $CONR^{2b.1}R^{2b.2}$;
  $R^{2b.1}$ is $C_{1-4}$-alkyl, $C_{0-4}$-alkyl-$C_{3-6}$-cycloalkyl, $C_{1-4}$-haloalkyl;
  $R^{2b.2}$ is H, $C_{1-4}$-alkyl;
  or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
and the remaining residues are defined as above.

Another aspect of the invention are co-crystals of compounds of formula 1, wherein
$R^1$ is $C_{1-6}$-alkyl, $C_{1-6}$-haloalkyl, O—$C_{1-6}$-haloalkyl, halogene;
m is 1 or 2;
$R^{2a}$ is H, $C_{1-4}$-alkyl;
$R^{2b}$ is H, $CONR^{2b.1}R^{2b.2}$;
  $R^{2b.1}$ is $C_{1-4}$-alkyl, $C_{0-4}$-alkyl-$C_{3-6}$-cycloalkyl, $C_{1-4}$-haloalkyl;
  $R^{2b.2}$ is H, $C_{1-4}$-alkyl;
  or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
$R^3$ is H, $C_{1-6}$-alkyl;
X is an anion selected from the group consisting of chloride or dibenzoyltartrate
j is 1 or 2.

Another aspect of the invention are co-crystals of compounds of formula 1, wherein
$R^{2a}$ is H, $C_{1-4}$-alkyl; preferably Methyl, Ethyl, Propyl;
$R^{2b}$ is H, $CONR^{2b.1}R^{2b.2}$;
  $R^{2b.1}$ is $C_{1-4}$-alkyl; preferably Methyl, Ethyl, Propyl;
  $R^{2b.2}$ is $C_{1-4}$-alkyl; preferably Methyl, Ethyl, Propyl;
and the remaining residues are defined as above.

Another aspect of the invention are co-crystals of compounds of formula 1, wherein
$R^{2a}$ is H, $C_{1-4}$-alkyl; preferably Methyl, Ethyl, Propyl;
$R^{2b}$ is H, $CONR^{2b.1}R^{2b.2}$;
  $R^{2b.1}$ is $C_{0-4}$-alkyl-$C_{3-6}$-cycloalkyl;
  $R^{2b.2}$ is H, $C_{1-4}$-alkyl; preferably H, Methyl, Ethyl, Propyl;
and the remaining residues are defined as above.

Another aspect of the invention are co-crystals of compounds of formula 1, wherein
$R^{2a}$ is H, $C_{1-4}$-alkyl; preferably Methyl, Ethyl, Propyl;
$R^{2b}$ is H, $CONR^{2b.1}R^{2b.2}$;
  $R^{2b.1}$ is $C_{1-4}$-haloalkyl;
  $R^{2b.2}$ is H, $C_{1-4}$-alkyl; preferably H, Methyl, Ethyl, Propyl;
and the remaining residues are defined as above.

Another aspect of the invention are co-crystals of compounds of formula 1, wherein
$R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
and the remaining residues are defined as above.

Another aspect of the invention are co-crystals of compounds of formula 1, wherein $R^1$, m, $R^{2a}$, $R^{2b}$, $R^3$, X and j are defined as above and the co-crystal former is selected from the group consisting of ascorbic acid, mucic acid, pamoic acid, succinamide, nicotinic acid, nicotinamide, isonicotinamide, l-lysine, l-proline, or hydrates or hydrochlorides of the same.

Another aspect of the invention are co-crystals of compounds of formula 1a, wherein $R^{2a}$, $R^{2b}$, $R^3$, X and j are defined as above

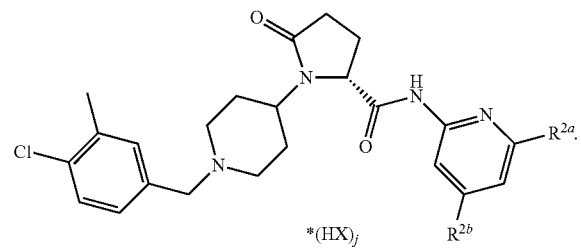

1a

Another aspect of the invention are co-crystals of compounds of formula 1a, wherein
$R^{2a}$ is H, $C_{1-4}$-alkyl; preferably Methyl, Ethyl, Propyl;
$R^{2b}$ is H, $CONR^{2b.1}R^{2b.2}$;
  $R^{2b.1}$ is $C_{1-4}$-alkyl; preferably Methyl, Ethyl, Propyl;
  $R^{2b.2}$ is $C_{1-4}$-alkyl; preferably Methyl, Ethyl, Propyl;
and the remaining residues are defined as above.

Another aspect of the invention are co-crystals of compounds of formula 1a, wherein
$R^{2a}$ is H, $C_{1-4}$-alkyl; preferably Methyl, Ethyl, Propyl;
$R^{2b}$ is H, $CONR^{2b.1}R^{2b.2}$;
  $R^{2b.1}$ is $C_{0-4}$-alkyl-$C_{3-6}$-cycloalkyl;
  $R^{2b.2}$ is H, $C_{1-4}$-alkyl; preferably H, Methyl, Ethyl, Propyl;
and the remaining residues are defined as above.

Another aspect of the invention are co-crystals of compounds of formula 1a, wherein
$R^{2a}$ is H, $C_{1-4}$-alkyl; preferably Methyl, Ethyl, Propyl;
$R^{2b}$ is H, $CONR^{2b.1}R^{2b.2}$;
  $R^{2b.1}$ is $C_{1-4}$-haloalkyl;
  $R^{2b.2}$ is H, $C_{1-4}$-alkyl; preferably H, Methyl, Ethyl, Propyl;
and the remaining residues are defined as above.

Another aspect of the invention are co-crystals of compounds of formula 1a, wherein
$R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
and the remaining residues are defined as above.

The free bases of compounds of formula 1 (j=0) are often amorphous and are used for a process of manufacturing co-crystal, nevertheless salts of compounds of formula 1 are preferred for a process of manufacturing co-crystal. Thus, another aspect of the invention are salts of compounds of formula 1 wherein $R^1$, m, $R^{2a}$, $R^{2b}$, $R^3$ are defined as for the co-crystals above and
X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate; preferably chloride, or dibenzoyltartrate
j is 0, 0.5, 1, 1.5 or 2; preferably 1 or 2.

Another aspect of the invention are salts of compounds of formula 1, wherein $R^1$, m, $R^{2a}$, $R^{2b}$, $R^3$ are defined as for the co-crystals above and
X is an anion selected from the group consisting of chloride or dibenzoyltartrate
j is 1 or 2.

Another aspect of the invention are salts of compounds of formula 1, wherein $R^1$, m, $R^{2a}$, $R^{2b}$, $R^3$ are defined as for the salts above and X is chloride and j is 2.

Another aspect of the invention are salts of compounds of formula 1, wherein $R^1$, m, $R^{2a}$, $R^{2b}$, $R^3$ are defined as for the salts above and X is dibenzoyltartrate and j is 1.

Another aspect of the invention are salts of compounds of formula 1a, wherein $R^{2a}$, $R^{2b}$, $R^3$, X and j are defined as above

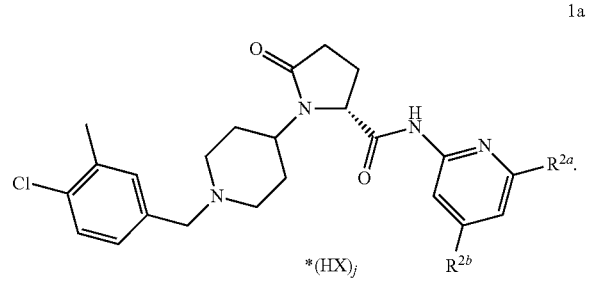

1a

Another aspect of the invention are salts of compounds of formula 1a, wherein
$R^{2a}$ is H, $C_{1-4}$-alkyl; preferably Methyl, Ethyl, Propyl;
$R^{2b}$ is H, $CONR^{2b.1}R^{2b.2}$;
   $R^{2b.1}$ is $C_{1-4}$-alkyl; preferably Methyl, Ethyl, Propyl;
   $R^{2b.2}$ is $C_{1-4}$-alkyl; preferably Methyl, Ethyl, Propyl;
and the remaining residues are defined as above.

Another aspect of the invention are salts of compounds of formula 1a, wherein
$R^{2a}$ is H, $C_{1-4}$-alkyl; preferably Methyl, Ethyl, Propyl;
$R^{2b}$ is H, $CONR^{2b.1}R^{2b.2}$;
   $R^{2b.1}$ is $C_{0-4}$-alkyl-$C_{3-6}$-cycloalkyl;
   $R^{2b.2}$ is H, $C_{1-4}$-alkyl; preferably H, Methyl, Ethyl, Propyl;
and the remaining residues are defined as above.

Another aspect of the invention are salts of compounds of formula 1a, wherein
$R^{2a}$ is H, $C_{1-4}$-alkyl; preferably Methyl, Ethyl, Propyl;
$R^{2b}$ is H, $CONR^{2b.1}R^{2b.2}$;
   $R^{2b.1}$ is $C_{1-4}$-haloalkyl;
   $R^{2b.2}$ is H, $C_{1-4}$-alkyl; preferably H, Methyl, Ethyl, Propyl;
and the remaining residues are defined as above.

Another aspect of the invention are salts of compounds of formula 1a, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
and the remaining residues are defined as above.

Another aspect of the invention are salts of compounds of formula 1a, wherein $R^1$, m, $R^{2a}$, $R^{2b}$, $R^3$, are defined as for the salts above and X is chloride and j is 2.

Another aspect of the invention are salts of compounds of formula 1a, wherein $R^1$, m, $R^{2a}$, $R^{2b}$, $R^3$ are defined as for the salts above and X is dibenzoyltartrate and j is 1. Another aspect of the invention are salts of compounds of formula 1a, wherein $R^1$, m, $R^{2a}$, $R^{2b}$, $R^3$ are defined as for the salts above and X is (S)—(S)-(+)-2,3-dibenzoyl-tartrate and j is 1.

The above mentioned salts are also useful for manufacturing a medicament for the prevention and/or treatment of diseases wherein the activity of a CCR3-receptor is involved.

Another aspect of the invention are co-crystals or salts of the compounds of the examples 1 to 36 from the—Synthesis of Examples—section below with an acid $(HX)_j$ wherein X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate; preferably chloride or dibenzoyltartrate and j is 0, 0.5, 1, 1.5 or 2; preferably 1 or 2; and in case of the co-crystals with a co-crystal former selected from the group consisting of orotic acid, hippuric acid, L-pyroglutamic acid, D-pyroglutamic acid, nicotinic acid, L-(+)-ascorbic acid, saccharin, piperazine, 3-hydroxy-2-naphtoic acid, mucic (galactaric) acid, pamoic (embonic) acid, stearic acid, cholic acid, deoxycholic acid, nicotinamide, isonicotinamide, succinamide, uracil, L-lysine, L-proline, D-valine, L-arginine, glycine, preferably ascorbic acid, mucic acid, pamoic acid, succinamide, nicotinic acid, nicotinamide, isonicotinamide, l-lysine, l-proline, Another aspect of the invention are co-crystals or salts of the compounds of the examples 1 to 36 from the—Synthesis of Examples—section below with an acid $(HX)_j$ wherein X is an anion selected from the group consisting of chloride or dibenzoyltartrate and j is 1 or 2; and in case of the co-crystals with a co-crystal former selected from the group consisting of ascorbic acid, mucic acid, pamoic acid, succinamide, nicotinic acid, nicotinamide, isonicotinamide, l-lysine, l-proline, Especially the dihydrochloride salt and the (S)—(S)-(+)-2,3-dibenzoyl-tartrate salts of a compound of formula 1, 1a or the examples 1 to 36 from the—Synthesis of Examples—section below are preferred examples of the invention which are useful for the preparation/manufacture of the above described co-crystals and/or for manufacturing a medicament for the prevention and/or treatment of diseases wherein the activity of a CCR3-receptor is involved.

In the context of this invention if dibenzoyltartrate is mentioned the preferred enantiomere of dibenzoyltartrate is always (S)—(S)-(+)-2,3-dibenzoyl-tartrate.

Another aspect of the invention are novel intermediates for manufacturing the compounds of formula 1. Those intermediates are obtainable from commercially available educts as described in the experimental section below.

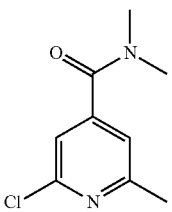

I12

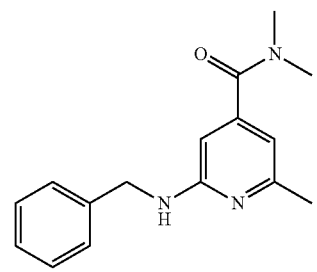

I13

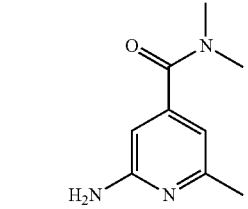

I14

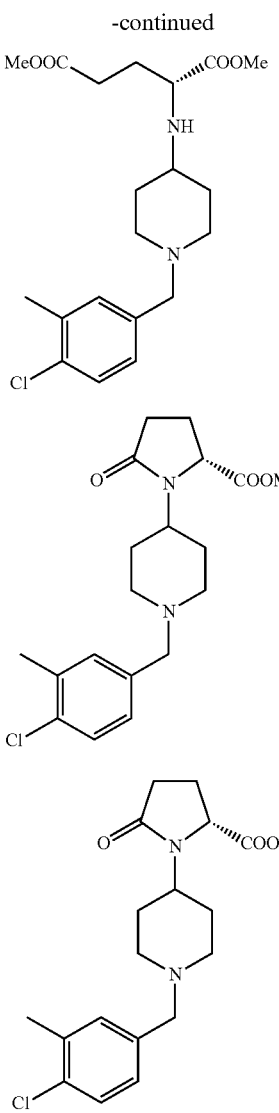

The apostrophe ' symbolizes in this context the difference between the name giving structure shown in the experimental section and the novel intermediate. The difference is that $R^1$ is restricted to Cl and Me and m is 1.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "$C_{1-3}$-alkyl-aryl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term halogene generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-haloalkyl", wherein n is an integer from 2 to n, either alone or in combination with another radical denotes an acyclic, saturated, branched or linear hydrocarbon radical with 1 to n C atoms wherein one or more hydrogen atoms are replaced by a halogene atom selected from among fluorine, chlorine or bromine, preferably fluorine and chlorine, particularly preferably fluorine. Examples include: $CH_2F$, $CHF_2$, $CF_3$.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes $-CH_2-$, $-CH_2-CH_2-$, $-CH(CH_3)-$, $-CH_2-CH_2-CH_2-$, $-C(CH_3)_2-$, $-CH(CH_2CH_3)-$, $-CH(CH_3)-CH_2-$, $-CH_2-CH(CH_3)-$, $-CH_2-CH_2-CH_2-CH_2-$, $-CH_2-CH_2-CH(CH_3)-$, $-CH(CH_3)-CH_2-CH_2-$, $-CH_2-CH(CH_3)-CH_2-$, $-CH_2-C(CH_3)_2-$, $-C(CH_3)_2-CH_2-$, $-CH(CH_3)-CH(CH_3)-$, $-CH_2-CH(CH_2CH_3)-$, $-CH(CH_2CH_3)-CH_2-$, $-CH(CH_2CH_2CH_3)-$, $-CH(CH(CH_3))_2-$ and $-C(CH_3)(CH_2CH_3)-$.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

PREPARATION

Preparation of Compounds of Formula 1

The examples of the present invention, represented by general structure 1, can be synthesized via methods 1 to 6 as outlined below where m, $R^1$, $R^{2a}$ and $R^{2b}$ are defined as above and $X^s$ is chloro or bromo and Y is methyl or ethyl. These methods are directly or indirectly dependent on Intermediate A which is synthesized according to scheme I. If not mentioned otherwise the starting materials are commercially available.

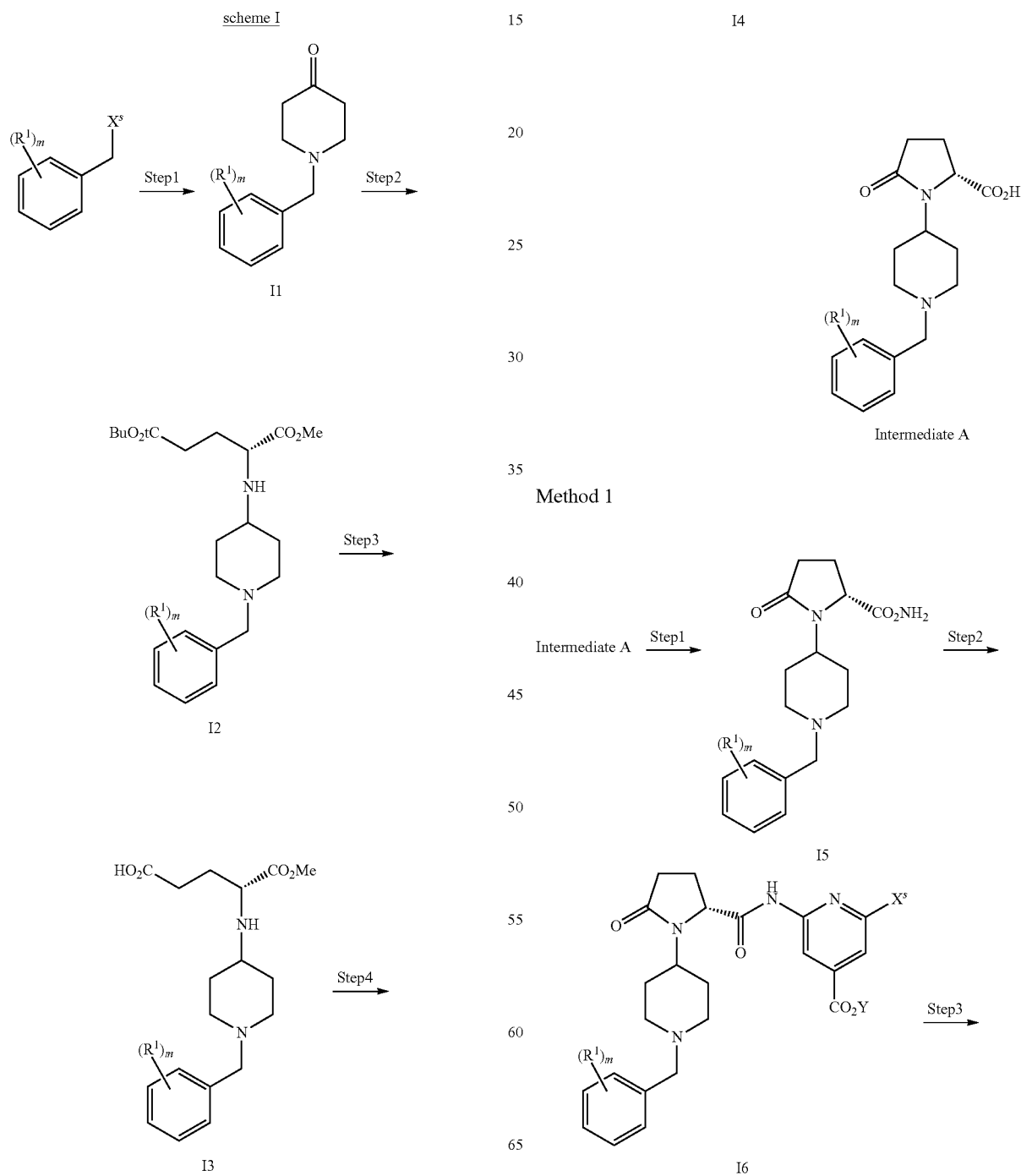

Method 1

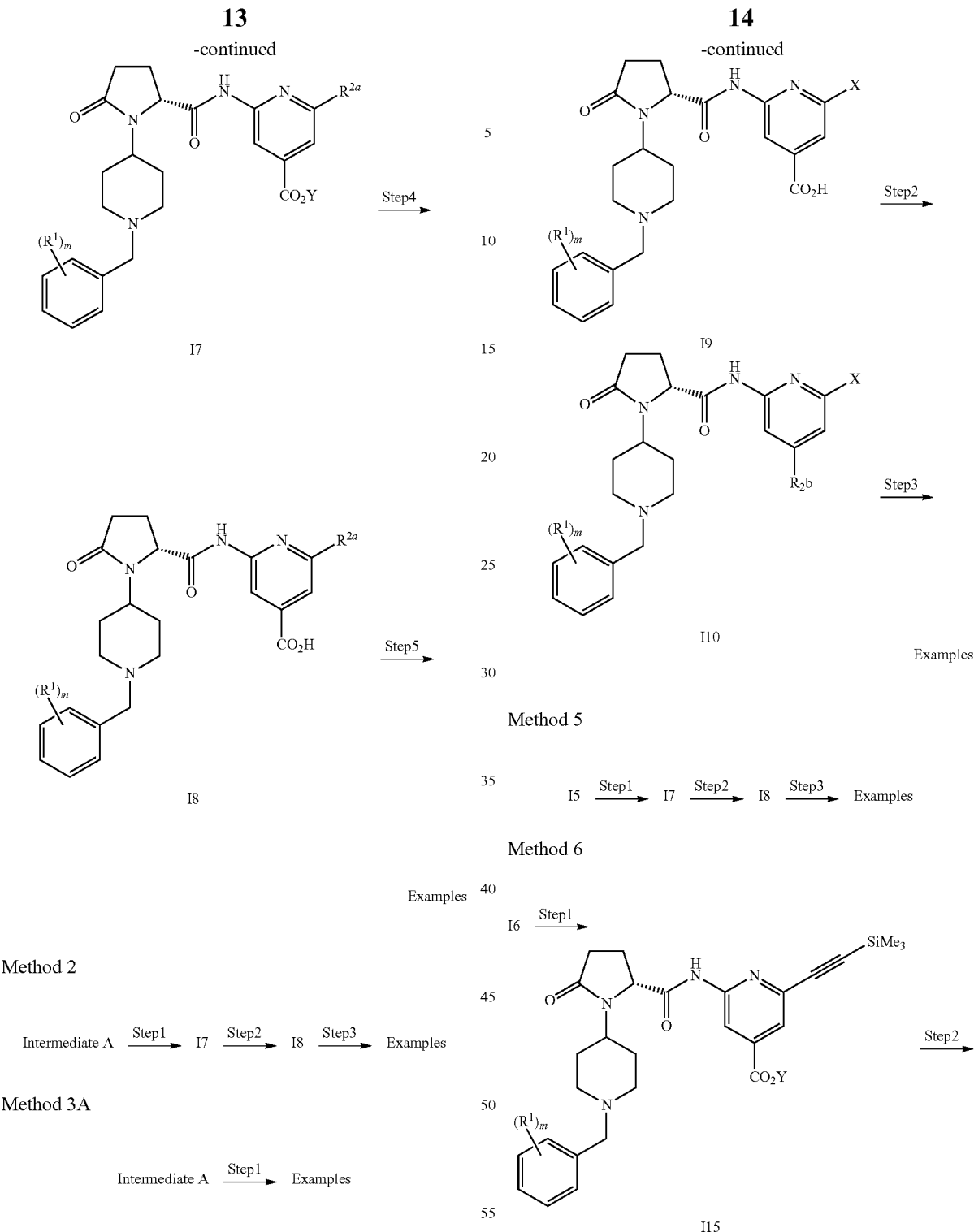

Method 2

Intermediate A →Step1→ I7 →Step2→ I8 →Step3→ Examples

Method 3A

Intermediate A →Step1→ Examples

Method 3B

Intermediate A →Step1→ I11 →Step2→ Examples

Method 4

I6 →Step1→

Method 5

I5 →Step1→ I7 →Step2→ I8 →Step3→ Examples

Method 6

Synthesis of Intermediate A (Exemplified with $R^1$ is 4-chloro-3-methyl)

Step 1: 4-Chloro-3-methyl benzylbromide (20 g) [synthesized according to literature: J. L. Kelley, J. A. Linn, J. W. T. Selway, *J. Med. Chem.* 1989, 32(8), 1757-1763], 4-Piperidone (22 g), $K_2CO_3$ (26 g) in acetonitrile (300 ml) is heated at 50° C. for 14 h. The suspension is filtered and the filtrate concentrated in vacuum. The residue is purified by flash chromatography (cyclohexane/EtOAc 1:1) to yield intermediate I1 (17.4 g).

Step 2: Intermediate I1 (10 g) and D-H-Glu(O'Bu)-OMe (10.8 g) are dissolved in DMF (200 ml) and HOAc (5 ml). Then molecular sieves (1.0 g, 4 Å, powder) are added and the suspension stirred overnight. Sodium triacetoxyborohydride (37.5 g) is added and the suspension stirred until complete conversion of the intermediate formed imine is observed. A basic pH is achieved by slow addition of aqueous NaHCO$_3$ solution before additional water and dichloromethane (500 mL) is added. The organic phase is separated and the water phase extracted with dichloromethane (500 ml). The organic phase is washed with brine, dried and concentrated in vacuum to yield intermediate I2 (19.5 g).

Step 3: Intermediate I2 (19.5 g, 74% purity) is dissolved in dichloromethane (40 ml) and trifluoroacetic acid (20 ml). The solution is stirred at 25° C. for 14 h before additional TFA (40 ml) is added and the solution continued stirring for further 7 h.

The reaction mixture is then concentrated in vacuum, dissolved in toluene and concentrated again to provide intermediate I3 (29.5 g).

Step 4: Intermediate I3 (29 g, purity 55%) is dissolved in a mixture of dichloromethane (100 ml) and DIPEA (22 ml). TBTU (15 g) is added and the solution is stirred for 30 min. Then dichloromethane (150 ml), water (100 ml) and saturated NaHCO$_3$ solution (100 ml) is added, the organic phase separated and the water phase extracted once with dichloromethane (100 ml). The organic phase is dried and concentrated to provide an oil which is then fractionated via reversed phase HPLC. The desired fractions are concentrated in vacuum, then a basic pH is adjusted with addition of NaHCO$_3$ solution and the product extracted with dichloromethane to provide intermediate I4 (8.1 g).

Step 5: Intermediate I4 (7 g) is dissolved in dioxane (50 ml). LiOH (2.5M aqueous solution, 23 ml) and water (20 ml) are added and stirred at room temperature overnight. The solution is acidified with aqueous 4N HCl and then concentrated in vacuum. The residue is dissolved in water, acetonitrile and a small amount of dioxane and lyophilised to provide of intermediate A (10.4 g, 71% purity).

Alternative Route to Intermediate A (Exemplified with R$^1$ is 4-chloro-3-methyl)

Step 1: 4-Chloro-3-methyl benzylchloride (85.7 g), 4-piperidone-hydrate-hydrochloride (80.5 g) and K$_2$CO$_3$ (141.8 g) are heated at reflux for 3.5 h in a 1:1 mixture of dioxane/water (600 ml). The suspension is cooled to room temperature and water (200 ml) is added. Afterwards, the mixture is extracted with toluene (2×400 ml). The combined organic phases are washed with brine (2×400 ml), dried over Na$_2$SO$_4$ and filtered. After evaporation to dryness, intermediate I1 [110.8 g, R$_f$=0.27 (TLC, silica, PE/EtOAc=7:3)] is obtained.

Step 2+3+4: D-H-Glu(OMe)-OMe*HCl (11.4 g) and intermediate I1 (11.4 g) are dissolved in DMF (35 ml) and stirred at room temperature for 2 h. Then, a solution of NaBH(OAc)$_3$ (36.8 g) in DMF (40 ml) is added at below 15° C. The mixture is warmed to room temperature and stirred for 30 minutes. Now a compound of formula I3'-Me

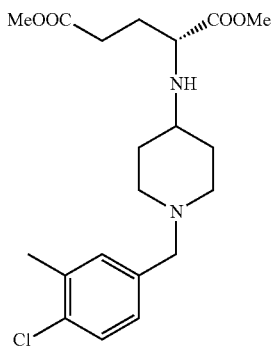

I3'-Me can be isolated or AcOH (0.3 ml) is added without isolation of a intermediate product and the mixture is heated to 105° C. for 1.5 h. The mixture is cooled to room temperature and cold water (188 ml) is added. The pH is adjusted to pH=8 by addition of NaOH (50% solution in water). Finally, the mixture is extracted with tert-butylmethylether (3×75 ml), the combined organic phases are washed with brine (1×50 ml), dried over Na$_2$SO$_4$ and filtered. After evaporation to dryness, intermediate I4 [15.9 g, ee=98.3%, R$_f$=0.30 (TLC, silica, toluene/EtOH=85:15)] is obtained.

Step 5: Intermediate I4 (150.3 g) is dissolved in MeOH (526 ml), 4N NaOH (145.7 ml) is added and the mixture is heated to reflux for 2 h. Afterwards, MeOH is distilled off and water (500 ml) is added. The mixture is extracted with tert-butylmethylether (2×300 ml). The aqueous phase is diluted with water (402 ml) and the pH is adjusted to pH=6.5 by addition of 4N HCl. The suspension is cooled to 5° C. and stirred for an additional 2 h. Finally, the mixture is filtered, the residue washed with water and dried to yield intermediate A [107.8 g, ee≥99.0%, m.p.: 260±3° C., R$_f$=0.2 (TLC, silica, toluene/EtOH=9:1]).

SYNTHESIS OF EXAMPLES

Synthesis of Examples via Method 1 (Exemplified with R$^1$ is 4-chloro-3-methyl; R$^{2a}$ is ethyl; R$^{2b}$ is N,N-dimethylcarboxamido; X$^S$ is bromo; Y is methyl;

Step 1: Intermediate A, as its N,N-diisopropylethylamine salt (500 mg), is suspended in dry DMF (7 ml) under inert atmosphere and TBTU (836 mg) is added, followed by N,N-diisopropylethylamine (0.53 ml). After stirring for 1 h at room temperature, hexamethyldisilazane (0.44 ml) is added and the mixture is stirred for 6 h. Further portions of TBTU (334 mg) and hexamethyldisilazane (0.22 ml) are added and the reaction is stirred for a further 18 h. The solvent is evaporated under reduced pressure and residue partitioned between saturated aqueous solution of NaHCO$_3$ and EtOAc. The layers are separated and the aqueous phase extracted with EtOAc. The combined organic extracts are washed with brine, dried under Na$_2$SO$_4$, filtered and the solvent is evaporated under reduced pressure. The crude is purified by flash chromatography (20 g Isolute® silica gel cartridge; eluent: dichloromethane/MeOH/NH$_4$OH 95/5/0.5) affording I5 (295 mg). UPLC(R$_t$)= 1.24 min (method M)

Step 2: To a stirred solution of citrazinic acid (15 g) is added phosphorous oxybromide (45 g) and the mixture heated to 140° C. After 14 h the mixture is cooled to 0° C. and MeOH (100 ml) added carefully under vigorous stirring. The mixture is then poured into a cooled (0° C.) aqueous sodium carbonate solution (1M, 500 ml), and chloroform (500 ml) is added. The biphasic mixture is filtered and the organic layer separated. After filtering through charcoal, the solution is concentrated in vacuum. The residue is purified by MPLC (dichloromethane:MeOH 100:3 to 100:6) to yield methyl 2,6-dibromoisonicotinate (13.7 g). HPLC(R$_t$)=1.62 (method D). To a stirred solution of I5 (2.6 g) in dioxane (30 ml) under argon is added methyl 2,6-dibromoisonicotinate (2.2 g), palladium acetate (167 mg), Xanthphos (432 mg) and Cs$_2$CO$_3$ (5.6 g) and the mixture refluxed for 1 h. The mixture is allowed to cool to room temperature and then added to water and extracted with EtOAc. The organic extracts are washed with brine, dried under Na$_2$SO$_4$, filtered and the solvent evaporated under reduced pressure. The crude product is purified by HPLC (Method E) affording I6 (0.6 g).

Step 3: To a stirred solution of I5 (500 mg) in dioxane (10 ml) under Argon is added 1,1'-bis(diphenylphosphino)ferrocenedichloropalladium(II) (65 mg) and diethylzinc (1M in hexane, 1.1 ml). The mixture is refluxed for 2 h then allowed to cool to rt. It is then quenched with NH₄Cl(aq) and extracted with EtOAc. The organic extracts are washed with brine, dried under Na₂SO₄, filtered, and the solvent evaporated under reduced pressure affording I7.

Step 4: (The procedure for Step 5 in the synthesis of Intermediate A is utilised with a reaction temperature of 50° C.). I8 is afforded (137 mg). HPLC($R_t$)=1.32 min (method D).

Step 5: To a stirred solution of I8 (800 mg) in DMF (10 ml) is added TBTU (772 mg), DIPEA (0.7 ml) and dimethylamine (0.36 g). After 2 h the reaction is quenched with water and extracted with EtOAc. The organic extracts are washed with brine, dried under Na₂SO₄, filtered, and the solvent evaporated under reduced pressure affording example 25 (410 mg). HPLC($R_t$)=1.32 min (method D).

Synthesis of Examples via Method 2 (Exemplified with $R^1$ is 4-chloro-3-methyl; $R^{2a}$ is hydrogen; $R^{2b}$ is N-methylcarboxamido; Y is ethyl).

Step 1: To a stirred solution of Intermediate A (0.48 g) in dichloromethane (5 ml) is added oxalylchloride (2M in dichloromethane, 2.5 ml). After 2 h, the reaction mixture is concentrated under reduced pressure. A suspension of 2-amino-isonicotinic ethyl ester (0.51 g) in pyridine (1 ml) and dioxane (2 ml) is added to the reaction mixture and this stirred for 10 min. The mixture was concentrated under reduced pressure to afford I7 (0.3 g). HPLC($R_t$)=1.37 min (method D).

Step 2: (The procedure for Step 5 in the synthesis of Intermediate A was utilised). I8 was afforded (55 mg). HPLC($R_t$)=1.23 min (method D).

Step 3: To a stirred solution of I8 (55 mg) at room temperature is added HATU (60 mg), DMF (1 ml) and DIPEA (0.07 ml). After 5 min methylamine (2M in THF, 0.2 ml) is added. After another 5 min, water is added and the mixture acidified with TFA. The crude product is purified by HPLC affording example 8 (50 mg). HPLC ($R_t$)=1.22 min (method D).

2-Amino-6-methylisonicotinic acid methyl ester also relevant for Step 1 is prepared as follows:

Step a: 2-chloro-6-methylisonicotinic acid (9 g), of aq ammonia (44 ml), of Cu(II)SO₄ (0.9 g) and of sodium sulphide (0.32 g) are added to an autoclave and heated to 155° C. overnight. The crude product is suspended in water to yield 2-amino-6-methylisonicotinic acid (3.6 g). HPLC: $R_t$=0.37 min (method D)

Step b: To 50 ml of MeOH is added drop wise acetyl chloride (3 ml) at room temperature. After 15 min, 2-amino-6-methylisonicotinic acid (2.3 g) is added and the mixture is stirred overnight at 50° C. After concentrating the solution, the resulting residue is suspended in acetone and then filtered and dried at 50° C. in vacuum, to yield 2-amino-6-methylisonicotinic acid methyl ester (4.1 g). HPLC: $R_t$=0.91 min (method D)

Synthesis of Examples via Method 3A (Exemplified with $R^1$ is 4-chloro-3-methyl; $R^{2a}$ is methyl; $R^{2b}$ is N,N-dimethylcarboxamido).

Step 1: Intermediate A (8.30 g), 2-amino-6,N,N-trimethylisonicotinamide (4.24 g) and NEt₃ (43 ml) are mixed in THF$_{abs}$. (66 ml) and heated to 55° C. T3P (50% solution in EtOAc, 56 ml) is added and the reaction mixture is stirred 1 h. After cooling to room temperature EtOAc (66 ml) and water (50 ml) is added. The phases are separated and the aqueous phase is extracted with EtOAc (1×50 ml). The combined organic phases are washed with brine and dried over Na₂SO₄. After filtration, the solvent is removed in vacuum to yield example 11 [9.78 g, $R_f$=0.55 (TLC, silica, toluene/EtOH=3:2)].

Synthesis of Dibenzoyltartrate Salt

Example 11 (200 mg), EtOH (0.8 ml) and water (0.4 ml) are mixed and heated to 70° C. A solution of (S)—(S)-(+)-2,3-dibenzoyl-tartaric acid (175 mg) in EtOH (0.6 ml) and water (0.6 ml) is added. After cooling to room temperature the precipitate is filtered, washed with EtOH/H₂O (7:3) and dried to afford the (S)—(S)-(+)-2,3-dibenzoyl-tartrate of example 11 (200 mg).

Synthesis of Examples via Method 3B (Exemplified with $R^1$ is 4-chloro-3-methyl; $R^{2a}$ is methyl; $R^{2b}$ is N,N-dimethylcarboxamido).

Step 1: Intermediate A (73.3 g) and NEt₃ (117 ml) are mixed in dry THF (440 ml) and T3P (50% solution in EtOAc, 246 ml) is added. The mixture is warmed to 50° C. for 30 minutes and 2-Amino-6-methylisonicotinic acid methyl ester (34.7 g) is added. After stirring over night, the reaction mixture is cooled to room temperature and water (440 ml) and 4N NaOH (52 ml) are added. The phases are separated and the aqueous phase is extracted with iPrOAc (2×220 ml). The combined organic phases are washed with water (2×220 ml), dried over Na₂SO₄, filtered and evaporated to dryness to a yield intermediate I11. [99.1 g, m.p.: 155±3° C., $R_f$=0.29 (TLC, silica, toluene/EtOH=85:15)].

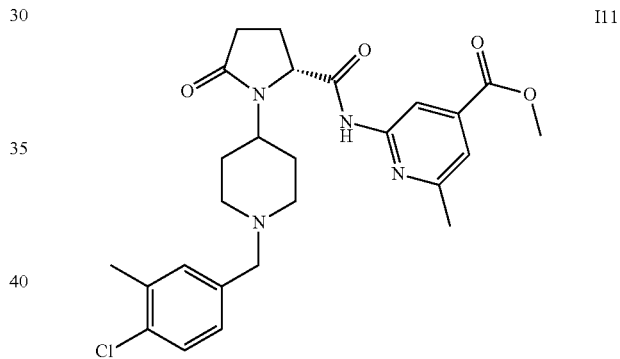

I11

Step 2: Intermediate I11 (138.6 g) is suspended in iPrOH (415 ml) and NaOH (50% solution in water, 14.5 ml) is added. The mixture is heated to 55° C. for 1 h. Afterwards, the solvent is removed in vacuum and the residue is co-distilled with iPrOH (2×200 ml) and MeTHF (1×500 ml). Then, dry MeTHF (701 ml), Me₂NH (2M solution in THF, 208 ml) and NEt₃ (117 ml) are added and the mixture is warmed to 50° C. T3P (50% solution in EtOAc, 327.4 ml) is added and the reaction mixture is stirred for an additional 1.5 h at 50° C. After cooling to room temperature water (818 ml) is added. The phases are separated and the aqueous phase is extracted with iPrOAc (2×281 ml). The combined organic phases are washed with water (2×281 ml), dried over Na₂SO₄, filtered and evaporated to dryness. The residue (crude example 11) is dissolved in acetone (1.46 L) and HCl (2.98 M solution in EtOAc, 240 ml) is dosed. The suspension is stirred for 1 h at room temperature. The precipitate is filtered off, washed with acetone (100 ml) and suspended in a mixture of acetone (1.53 L) and EtOH$_{abs}$. (180 ml) for 30 minutes at 50° C. The suspension is then cooled to 10° C. and stirred for 30 minutes. The precipitate is filtered off, washed with cold acetone (200 ml) and dried intense to yield example 11 as dihydrochloride salt (117 g, ee≥99.9%, m.p.: 194±5° C.), optionally the product may also exists as hydrate of the dihydrochloride of example 11 without defined melting point.

Synthesis of 2-amino-6,N,N-trimethylisonicotinamide

Step 1: 2-Chloro-6-methyl-isonicotinic acid [Lit.: Sperber et al., *JACS* 1959, 81, 704-707] (96.1 g) is suspended in toluene (480 ml) and DMF (0.5 ml) is added. After warming to 85° C. SOCl$_2$ (61.5 ml) is dosed. The reaction mixture is heated to reflux for 1.5 h and then cooled to room temperature. After removal of solvent and excess reagent in vacuum, the residue is co-distilled with toluene (2×200 ml) and finally dissolved in toluene (300 ml). Afterwards, the above prepared solution is added to a mixture of Me$_2$NH (2M solution in THF, 336 ml) and NEt$_3$ (94 ml) at below 10° C. The mixture is warmed to room temperature and stirred for an additional 30 minutes. Water (300 ml) is added and the mixture is extracted with toluene (3×200 ml). The combined organic phases are washed with brine (1×200 ml), dried over Na$_2$SO$_4$, filtered and evaporated. The oily residue is treated with n-heptane (288 ml) and seeds are added. After stirring 30 minutes at room temperature, the precipitate is filtered off, washed and dried in vacuum to yield intermediate I12 [93.7 g, m.p.: 85±3° C., R$_f$=0.22 (TLC, silica, PE/EtOAc=1:1)].

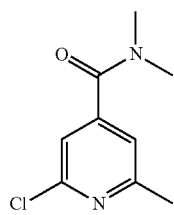

I12

Step 2: Intermediate I12 (26.7 g), Cs$_2$CO$_3$ (70 g), Pd(OAc)$_2$ (302 mg) and (2-Biphenyl)-di-tert.-butylphosphin (0.92 g) are mixed in dioxane$_{abs.}$ (270 ml) and benzyl amine (22.3 ml) is added. The reaction mixture is heated to 100° C. over night, cooled to room temperature and filtered. Aqueous HCl (2M, 100 ml) is added and the mixture extracted with t-butylmethylether (70 ml). To the aqueous phase NaOH (4N, 55 ml) is added. After extraction with tert-butylmethylether (3×70 ml) the combined organic phases are washed with brine, dried over Na$_2$SO$_4$, filtered and evaporated to dryness to yield intermediate I13 [23.0 g, m.p.: 124±3° C., R$_f$=0.20 (TLC, silica, PE/EtOAc=2:3)].

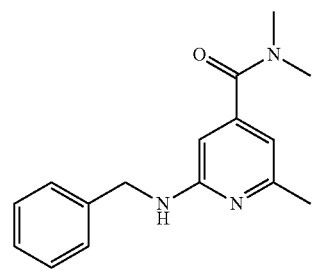

I13

Step 3: Intermediate I13 (37.0 g) and Pd(OH)$_2$/C are suspended in EtOH$_{abs.}$ (185 ml), and AcOH (16 ml). The mixture is hydrogenated at 70° C. and 60 psi until complete consumption. The mixture is filtered and the filtrate is evaporated to dryness. The remaining residue is dissolved in dichloromethane (250 ml), washed with Na$_2$CO$_3$-solution (10% in water, 150 ml) and dried over Na$_2$SO$_4$. After filtration and evaporation 2-amino-6,N,N-trimethylisonicotinamide I14 is isolated [22.2 g, m.p.: 168±3° C., R$_f$=0.15 (TLC, silica, deactivated with NEt$_3$/PE, EtOAc)].

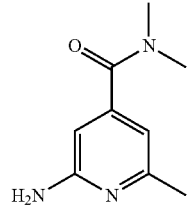

I14

Alternative: Intermediate I12 (26.6 g), Cs$_2$CO$_3$ (48.9 g), benzophenonimine (25.0 g), Pd(OAc)$_2$ (0.60 g) and racemic BINAP (4.52 g) are suspended in toluene (266 ml) and heated to 100° C. for 2 days. The mixture is cooled to room temperature and filtered. 4N HCl (67 ml) is added to the filtrate and the mixture is stirred for 30 minutes at room temperature. Water (67 ml) is added and the phases are separated. The organic phase is extracted with water (50 ml). The combined aqueous phases are washed with toluene (100 ml). After addition of 4N NaOH (70 ml) the alkaline aqueous phase is extracted with CH$_2$Cl$_2$ (4×100 ml). The combined organic phases are washed with brine (100 ml), dried over Na$_2$SO$_4$ and filtered. After evaporation to dryness, 2-amino-6,N,N-trimethylisonicotinamide I14 is isolated [22.1 g, R$_f$=0.15 (TLC, silica, deactivated with NEt$_3$/PE, EtOAc)].

Instead of benzyl amine (as in Step 1) or benzophenoimine (as in the Alternative) as described above further N-sources like CH$_3$CONH$_2$ oder CF$_3$CONH$_2$ can be used for the synthesis of synthesis of 2-amino-6,N,N-trimethylisonicotinamide.

Synthesis of Examples via Method 4 (Exemplified with R1 is 3-methyl-4-chloro; R$^{2a}$ is cyclopropyl; R$^{2b}$ is N,N-dimethylcarboxamido; X is bromo and Y is methyl).

Step 1: To a stirred solution of I6 (90 mg) in THF (3 ml) at room temperature is added LiOH (10% aqueous solution; 0.05 ml). After 1 h the reaction is heated to 30° C. and after a further 30 min, concentrated under reduced pressure affording I9 (110 mg). HPLC(R$_t$)=1.34 min (method D).

Step 2: To a stirred solution of I9 (80 mg) in dichloromethane (5 ml) containing a few drops of DMF at room temperature is added HATU (110 mg). After 45 min dimethylamine (0.014 ml) was added and the mixture stirred for 2 h. Additional HATU (110 mg) and dimethylamine (1 ml) are added and after 2 h the reaction is added to water/dichloromethane and phase separated via an Isolute HMN cartridge. The organic phase is dried under Na$_2$SO$_4$, filtered, and the solvent evaporated under reduced pressure. HPLC purification of the residue affords I10 (20 mg). HPLC(R$_t$)=1.32 min (method D).

Step 3: To a stirred solution of bromocyclopropane (0.039 ml) in THF at −78° C. under argon is added t-butyl lithium (0.056 ml) drop wise. After 25 min, cyclopropylzincbromide (0.5M in THF, 0.096 ml) is added and the mixture allowed to warm to rt. After 1 h I10 (23 mg) and 1,1'-bis(diphenylphosphino)ferrocenedichloropalladium(II) (3 mg). After a further 35 min, further cyclopropylzincbromide (0.5M in THF, 0.096 ml) is added and 1 h later further cyclopropyl zinc bromide (0.5M in THF, 0.096 ml) added and the mixture stirred overnight. Further cyclopropyl zinc bromide (0.5M in THF, 0.24 ml) is added and after 4 h the mixture is diluted with THF and filtered. HPLC purification affords example 32 (7 mg). HPLC (R$_t$)=1.34 min (method D).

Synthesis of Examples via Method 5 (Exemplified with R1 is 4-chloro-3-methyl; R$^{2a}$ is methoxy; R$^{2b}$ is N,N-dimethylcarboxamido; Y is methyl).

Step 1: A solution of sodium methoxide (375 mg) and methyl 2,6 dibromoisonicotinate (1.0 g) in MeOH (20 ml) is heated in a microwave oven at 130° C. for 30 min. Then additional sodium methoxide (281 mg) is added and heating continued for additional 15 min at 130° C. Concentrated sulphuric acid (1.86 ml) is then added to the reaction mixture and the resulting suspension is heated for 4 h at 80-85° C. After cooling to room temperature, the mixture is poured into an ice cold aqueous sodium carbonate solution (100 mL) and extracted with dichloromethane (100 ml). The organic layer is separated, dried over Na$_2$SO$_4$ and concentrated in vacuum. The residue is purified by MPLC (dichloromethane:MeOH=100:3 to 100:5) to yield 710 mg of a 7:3 mixture of 2-bromo-6-methoxyisonicotinate (497 mg) and the corresponding trimethyl citrazinic acid (213 mg). HPLC(R$_t$)=1.66 min (method D). This mixture is then used in a procedure analog to Step 2 in Method 1.

Steps 2+3: (Carried out analog to Steps 2, 3 respectively in Method 2)

Affords example 26 (7 mg). HPLC(R$_t$)=1.29 min (method D).

Synthesis of Examples via Method 6 (Exemplified with R1 is 4-chloro-3-methyl; R$^{2a}$ is ethynyl; R$^{2b}$ is N,N-dimethylcarboxamido; X is bromo; Y is methyl).

Step 1: To a solution of I6 (3.5 g) in THF (20 ml) at room temperature under argon is added TEA (2 ml), bistriphenylphosphinpalladiumchloride (219 mg) and copper(I)iodide (59 mg) followed by trimethylsilylacetylene (1 ml). After overnight stirring, the mixture was added to ice-water and extracted with EtOAc. The organic layer is separated, dried over Na$_2$SO$_4$ and concentrated in vacuum. Flash chromatography (95:5 dichloromethane:MeOH) affords I15 (3 g). R$_f$(95:5 dichloromethane:MeOH) 0.22.

Step 2: To a stirred solution of I15 (3 g) in dioxane (30 ml) at room temperature is added LiOH (1M aqueous solution, 10.4 ml). After 2 h, HCl (1M aqueous solution) is added to neutral pH and the resultant suspension is filtered and dried. HPLC purification affords I8 (with R$^{2a}$ is ethynyl) (2.3 g). HPLC(R$_t$)=1.31 min (method D)

Step 3: (Carried out analog to Step 3 of Method 2).

Affords example 34 (210 mg). HPLC(R$_t$)=1.23 min (method E)

The following examples can be synthesized according to the above methods:

| # Example | Structure | synth. Method | HPLC Method | HPLC Rt |
|---|---|---|---|---|
| 1 | 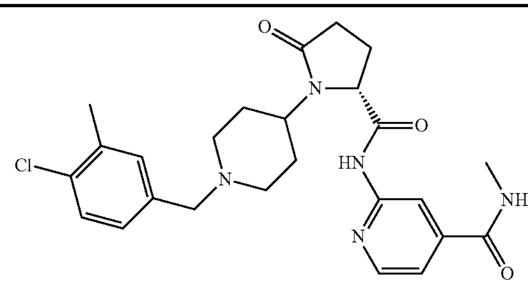 | 2 | d | 1.24 |
| 2 | 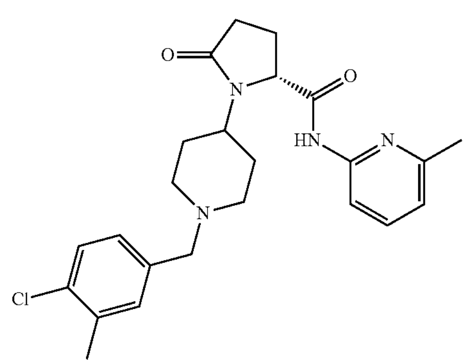 [SMILES: Cc1cccc(NC(=O)[C@H]2CCC(=O)N2C2CCN(Cc3ccc(Cl)c(C)c3)CC2)n1] | 3 | b | 1.49 |

-continued
| # Example | Structure | synth. Method | HPLC Method | HPLC Rt |
|---|---|---|---|---|
| 3 | 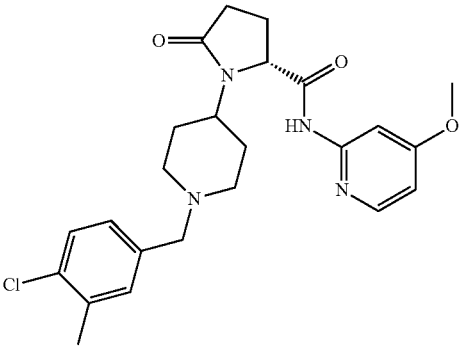 [SMILES: COc1ccnc(NC(=O)[C@H]2CCC(=O)N2C2CCN(Cc3ccc(Cl)c(C)c3)CC2)c1] | 3 | b | 1.36 |
| 4 | 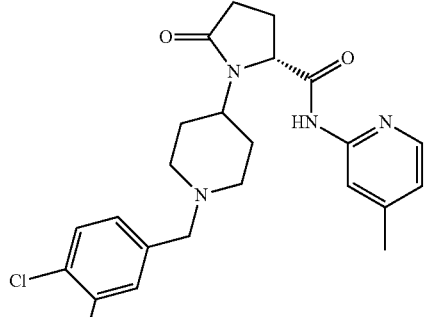 | 3 | B | 1.37 |
| 5 | 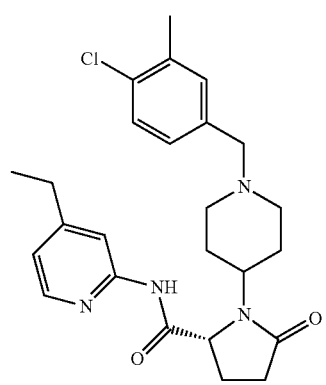 [SMILES: CCc1ccnc(NC(=O)[C@H]2CCC(=O)N2C2CCN(Cc3ccc(Cl)c(C)c3)CC2)c1] | 3 | B | 1.50 |
| 6 | 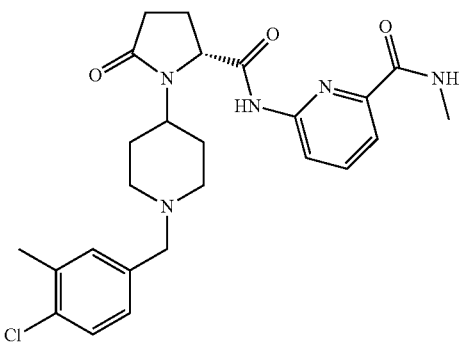 [SMILES: CNC(=O)c1cccc(NC(=O)[C@H]2CCC(=O)N2C2CCN(Cc3ccc(Cl)c(C)c3)CC2)n1] | 3 | D | 1.25 |

-continued

| # Example | Structure | synth. Method | HPLC Method | HPLC Rt |
|---|---|---|---|---|
| 7 | 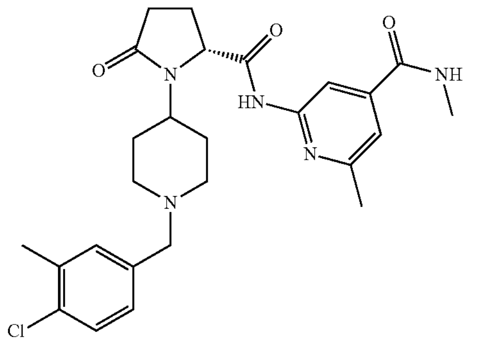 [SMILES: CNC(=O)c1cc(C)nc(NC(=O)[C@H]2CCC(=O)N2C2CCN(Cc3ccc(Cl)c(C)c3)CC2)c1] | 2 | d | 1.26 |
| 8 | 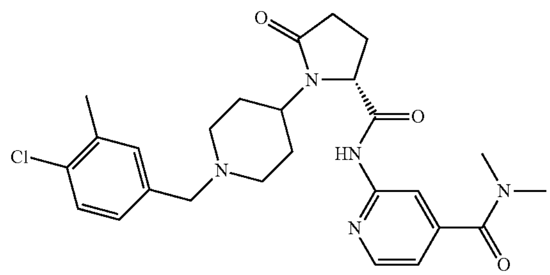 [SMILES: Cc1cc(CN2CCC(N3C(=O)CC[C@@H]3C(=O)Nc3cc(C(=O)N(C)C)ccn3)CC2)ccc1Cl] | 2 | d | 1.22 |
| 9 | 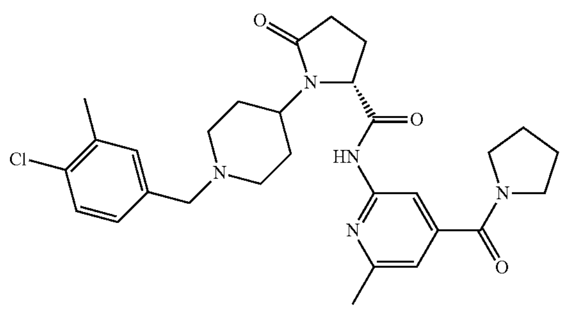 [SMILES: Cc1cc(C(=O)N2CCCC2)cc(NC(=O)[C@H]2CCC(=O)N2C2CCN(Cc3ccc(Cl)c(C)c3)CC2)n1] | 2 | D | 1.29 |
| 10 | 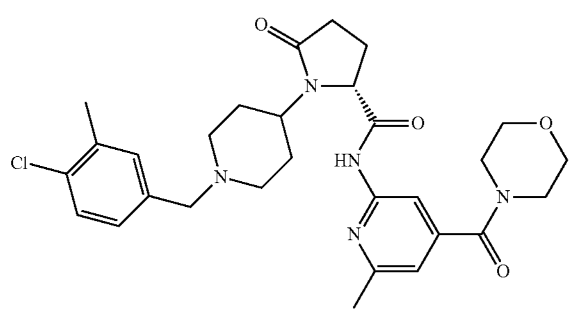 [SMILES: Cc1cc(C(=O)N2CCOCC2)cc(NC(=O)[C@H]2CCC(=O)N2C2CCN(Cc3ccc(Cl)c(C)c3)CC2)n1] | 2 | d | 1.26 |
| 11 | 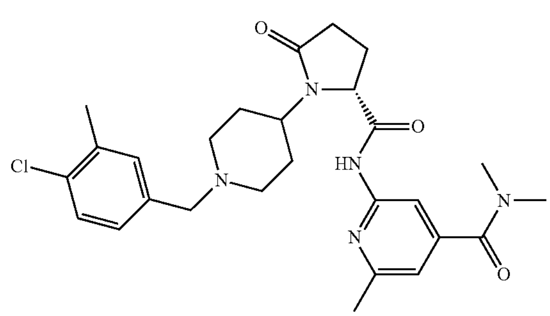 [SMILES: Cc1cc(C(=O)N(C)C)cc(NC(=O)[C@H]2CCC(=O)N2C2CCN(Cc3ccc(Cl)c(C)c3)CC2)n1] | 3 | d | 1.28 |

-continued

| # Example | Structure | synth. Method | HPLC Method | HPLC Rt |
|---|---|---|---|---|
| 12 | 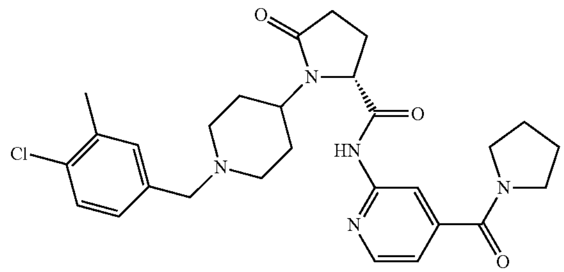 [SMILES: Cc1cc(CN2CCC(N3C(=O)CC[C@@H]3C(=O)Nc3cc(C(=O)N4CCCC4)ccn3)CC2)ccc1Cl] | 2 | d | 1.32 |
| 13 | 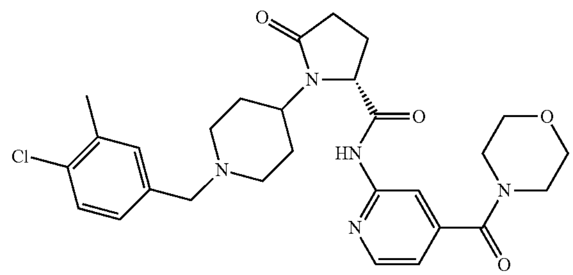 [SMILES: Cc1cc(CN2CCC(N3C(=O)CC[C@@H]3C(=O)Nc3cc(C(=O)N4CCOCC4)ccn3)CC2)ccc1Cl] | 2 | d | 1.24 |
| 14 | 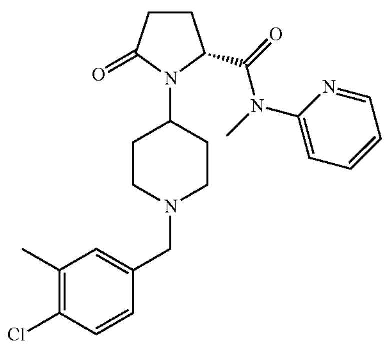 [SMILES: Cc1cc(CN2CCC(N3C(=O)CC[C@@H]3C(=O)N(C)c3ccccn3)CC2)ccc1Cl] | 3 | D | 1.27 |
| 15 | 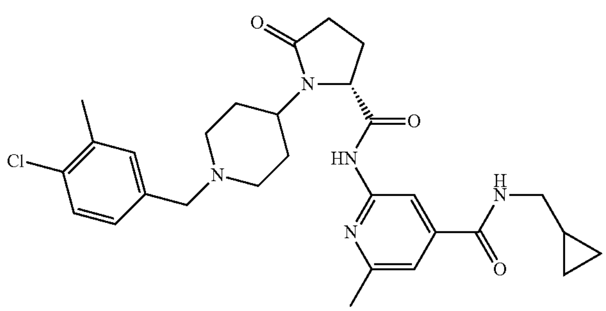 [SMILES: Cc1cc(C(=O)NCC2CC2)cc(NC(=O)[C@H]2CCC(=O)N2C2CCN(Cc3ccc(Cl)c(C)c3)CC2)n1] | 2 | D | 1.38 |
| 16 | 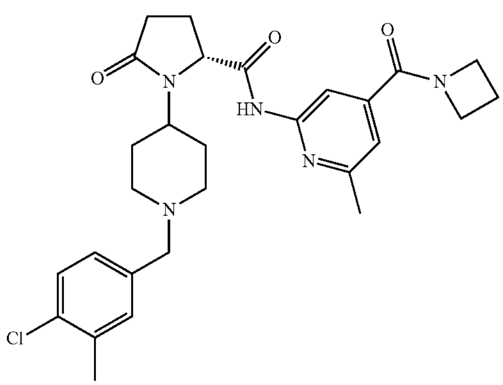 [SMILES: Cc1cc(C(=O)N2CCC2)cc(NC(=O)[C@H]2CCC(=O)N2C2CCN(Cc3ccc(Cl)c(C)c3)CC2)n1] | 2 | B | 1.53 |

-continued

| # Example | Structure | synth. Method | HPLC Method | HPLC Rt |
|---|---|---|---|---|
| 17 | 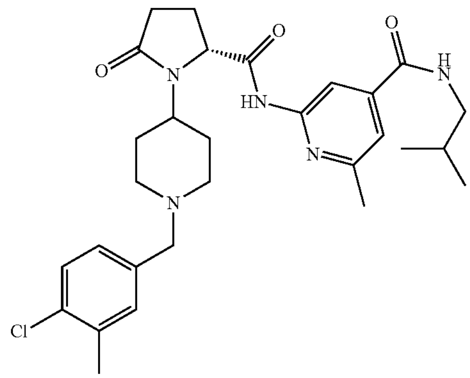 [SMILES: Cc1cc(C(=O)NCC(C)C)cc(NC(=O)[C@H]2CCC(=O)N2C2CCN(Cc3ccc(Cl)c(C)c3)CC2)n1] | 2 | B | 1.66 |
| 18 | 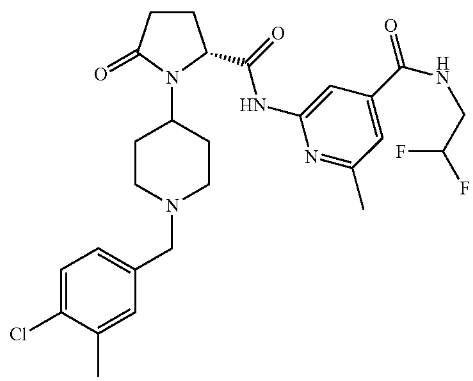 [SMILES: Cc1cc(C(=O)NCC(F)F)cc(NC(=O)[C@H]2CCC(=O)N2C2CCN(Cc3ccc(Cl)c(C)c3)CC2)n1] | 2 | B | 1.60 |
| 19 | 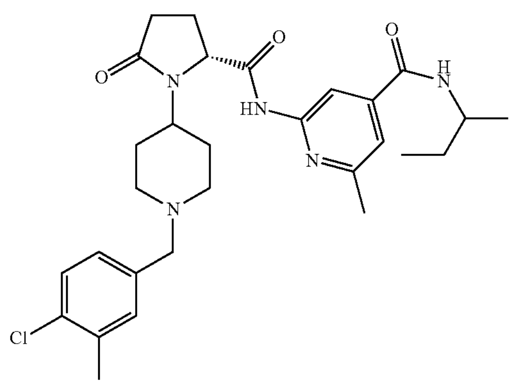 [SMILES: CCC(C)NC(=O)c1cc(C)nc(NC(=O)[C@H]2CCC(=O)N2C2CCN(Cc3ccc(Cl)c(C)c3)CC2)c1] | 2 | B | 1.65 |
| 21 | 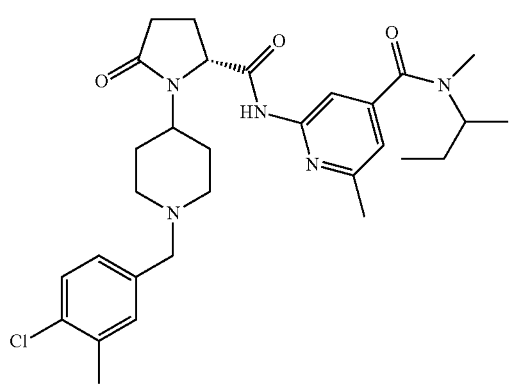 [SMILES: CCC(C)N(C)C(=O)c1cc(C)nc(NC(=O)[C@H]2CCC(=O)N2C2CCN(Cc3ccc(Cl)c(C)c3)CC2)c1] | 2 | B | 1.65 |

-continued
| # Example | Structure | synth. Method | HPLC Method | HPLC Rt |
|---|---|---|---|---|
| 22 | 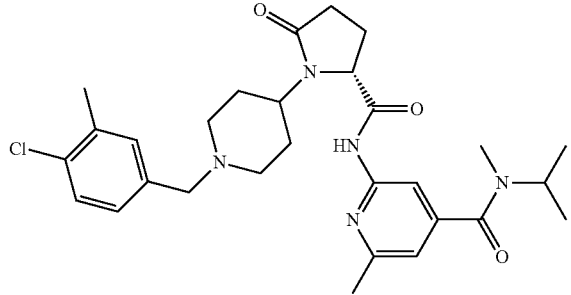 [SMILES: Cc1cc(C(=O)N(C)C(C)C)cc(NC(=O)[C@H]2CCC(=O)N2C2CCN(Cc3ccc(Cl)c(C)c3)CC2)n1] | 2 | D | 1.34 |
| 23 | 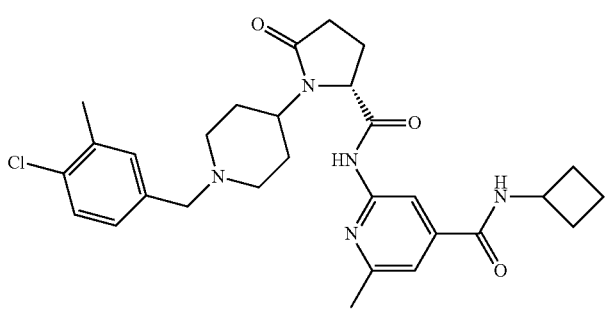 [SMILES: Cc1cc(C(=O)NC2CCC2)cc(NC(=O)[C@H]2CCC(=O)N2C2CCN(Cc3ccc(Cl)c(C)c3)CC2)n1] | 2 | D | 1.36 |
| 24 | 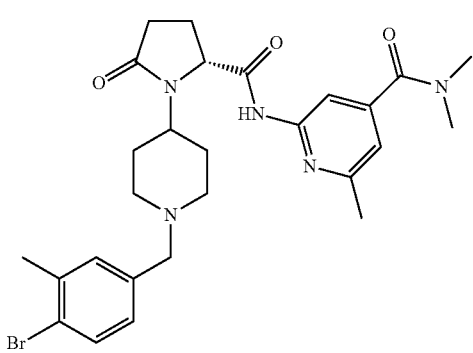 [SMILES: Cc1cc(C(=O)N(C)C)cc(NC(=O)[C@H]2CCC(=O)N2C2CCN(Cc3ccc(Br)c(C)c3)CC2)n1] | 2 | d | 1.28 |
| 25 | 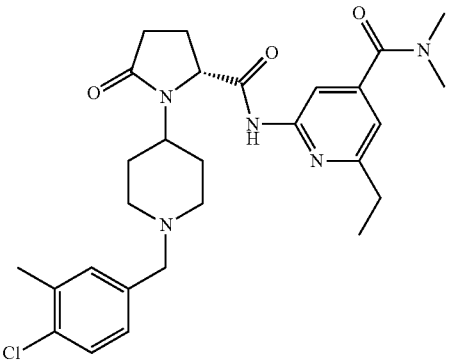 [SMILES: CCc1cc(C(=O)N(C)C)cc(NC(=O)[C@H]2CCC(=O)N2C2CCN(Cc3ccc(Cl)c(C)c3)CC2)n1] | 1 | d | 1.31 |

-continued
| # Example | Structure | synth. Method | HPLC Method | HPLC Rt |
|---|---|---|---|---|
| 26 | 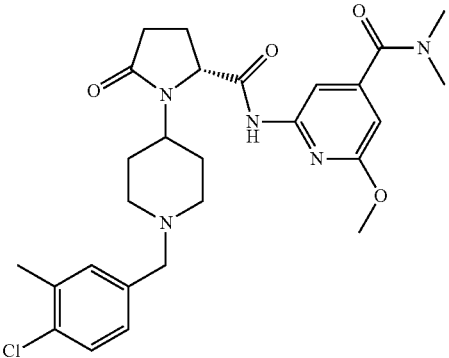 [SMILES: COc1cc(C(=O)N(C)C)cc(NC(=O)[C@H]2CCC(=O)N2C2CCN(Cc3ccc(Cl)c(C)c3)CC2)n1] | 5 | d | 1.29 |
| 27 | 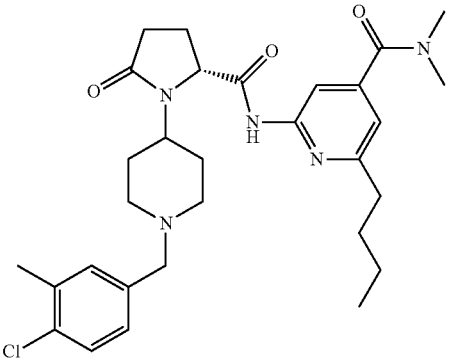 [SMILES: CCCCc1cc(C(=O)N(C)C)cc(NC(=O)[C@H]2CCC(=O)N2C2CCN(Cc3ccc(Cl)c(C)c3)CC2)n1] | 4 | d | 1.41 |
| 28 | 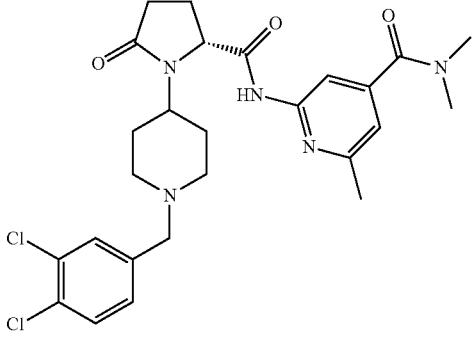 [SMILES: Cc1cc(C(=O)N(C)C)cc(NC(=O)[C@H]2CCC(=O)N2C2CCN(Cc3ccc(Cl)c(Cl)c3)CC2)n1] | 2 | d | 1.26 |
| 29 | 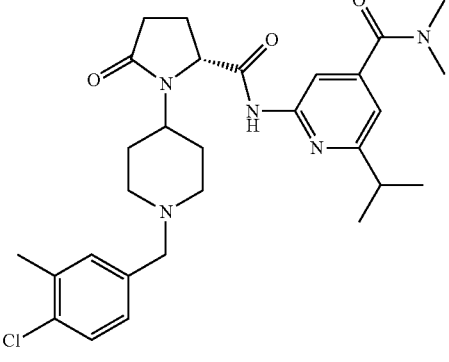 | 1 | d | 1.36 |

-continued

| # Example | Structure | synth. Method | HPLC Method | HPLC Rt |
|---|---|---|---|---|
| 30 | 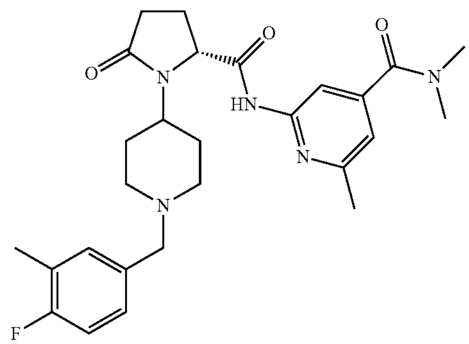 [SMILES: Cc1cc(C(=O)N(C)C)cc(NC(=O)[C@H]2CCC(=O)N2C2CCN(Cc3ccc(F)c(C)c3)CC2)n1] | 3 | D | 1.21 |
| 31 | 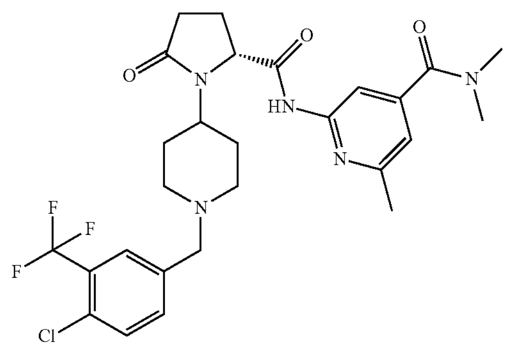 [SMILES: Cc1cc(C(=O)N(C)C)cc(NC(=O)[C@H]2CCC(=O)N2C2CCN(Cc3ccc(Cl)c(C(F)(F)F)c3)CC2)n1] | 3 | D | 1.30 |
| 32 | 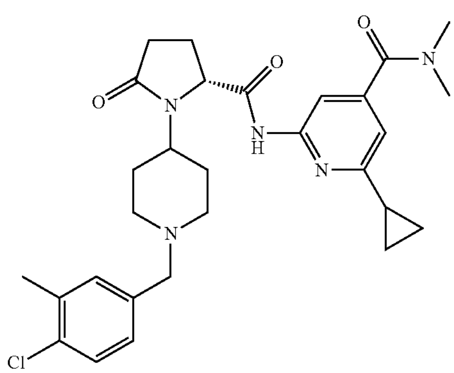 [SMILES: Cc1cc(CN2CCC(N3C(=O)CC[C@@H]3C(=O)Nc3cc(C(=O)N(C)C)cc(C4CC4)n3)CC2)ccc1Cl] | 4 | d | 1.34 |
| 33 | 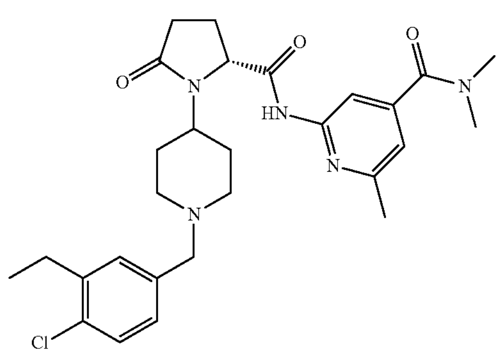 [SMILES: CCc1cc(CN2CCC(N3C(=O)CC[C@@H]3C(=O)Nc3cc(C(=O)N(C)C)cc(C)n3)CC2)ccc1Cl] | 3 | D | 1.30 |

| # Example | Structure | synth. Method | HPLC Method | HPLC Rt |
|---|---|---|---|---|
| 34 | 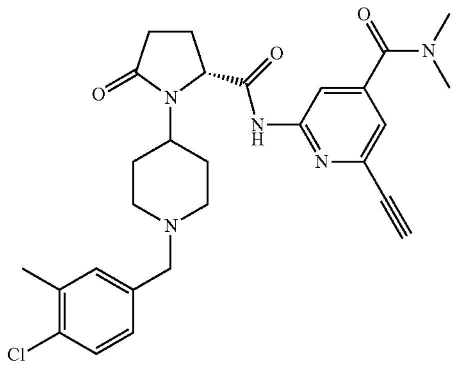 [SMILES: C#Cc1cc(C(=O)N(C)C)cc(NC(=O)[C@H]2CCC(=O)N2C2CCN(Cc3ccc(Cl)c(C)c3)CC2)n1] | 6 | e | 1.23 |
| 35 | 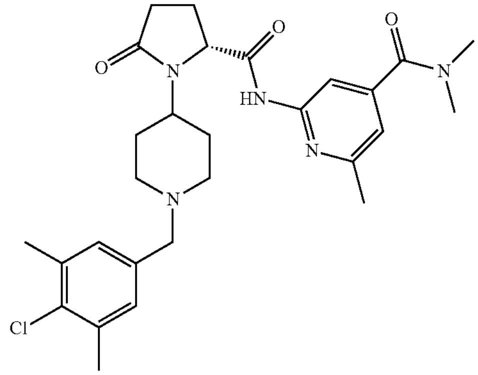 [SMILES: Cc1cc(C(=O)N(C)C)cc(NC(=O)[C@H]2CCC(=O)N2C2CCN(Cc3cc(C)c(Cl)c(C)c3)CC2)n1] | 3 | D | 1.31 |
| 36 | 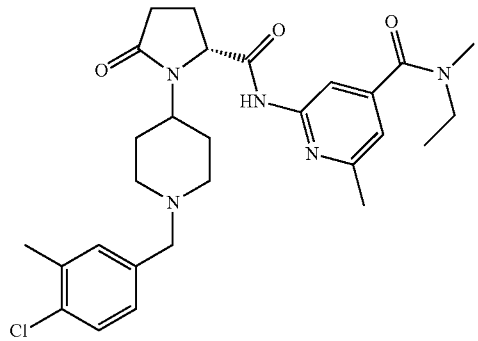 [SMILES: CCN(C)C(=O)c1cc(C)nc(NC(=O)[C@H]2CCC(=O)N2C2CCN(Cc3ccc(Cl)c(C)c3)CC2)c1] | 2 | E | 1.24 |

Examples of Co-Crystals

Other features and advantages of the present invention will become apparent from the following more detailed examples which illustrate, by way of example, the principles of the invention.

Synthesis of co-crystals starting from the dihydrochloride of compounds of formula 1: Equimolar amounts of the dihydrochloride of one compound of formula 1, preferably one of the Examples 1 to 19 and 21 to 36 above, and the appropriate co-crystal former (selected from orotic acid, hippuric acid, L-pyroglutamic acid, D-pyroglutamic acid, nicotinic acid, L-(+)-ascorbic acid, saccharin, piperazine, 3-hydroxy-2-naphtoic acid, mucic (galactaric) acid, pamoic (embonic) acid, stearic acid, cholic acid, deoxycholic acid, nicotinamide, isonicotinamide, succinamide, uracil, L-lysine, L-proline, D-valine, L-arginine, glycine) were combined in a proper solvent (chosen among e.g. 2-butanone, acetone, acetonitrile, isopropylacetate) at 80-50° C. After stirring 10-60 minutes the reaction mixture was cooled to room temperature, if needed additional solvent was added to facilitate the stirring of the mixture. Finally, the solid was recovered upon filtration, washed with a proper organic solvent and then dried in vacuum to yield the corresponding co-crystal.

Synthesis of co-crystals starting from the free base of compounds of formula 1: Equimolar amounts of the free base of one compound of formula 1, preferably one of the Examples 1 to 36 above, the appropriate co-crystal former (selected from orotic acid, hippuric acid, L-pyroglutamic acid, D-pyroglutamic acid, nicotinic acid, L-(+)-ascorbic acid, saccharin, piperazine, 3-hydroxy-2-naphtoic acid, mucic (galactaric) acid, pamoic (embonic) acid, stearic acid, cholic acid, deoxycholic acid, nicotinamide, isonicotinamide, succinamide, uracil, L-lysine, L-proline, D-valine, L-arginine, glycine) and hydrochloric acid (1.5-2 equiv.) were combined in a proper solvent (chosen among e.g. 2-butanone, acetone, acetonitrile, isopropylacetate) and the mixture set to 80-50° C. After stirring 10-60 minutes the mixture was cooled to room temperature, if needed additional solvent was added to facilitate the stirrability of the mixture. Finally the solid was recovered upon filtration, washed with a proper organic solvent and then dried in vacuum to yield the corresponding co-crystal.

Analytics of Exemplified Co-Crystals and Salts

The crystalline co-crystal forms and salts were characterised by an X-ray powder diffraction pattern, made using $CuK_{\alpha 1}$ radiation, which comprises peaks at specific degrees 2Θ (±0.05 degrees 2Θ).

The X-ray powder diffraction patterns are recorded, within the scope of the present invention, using a STOE-STADI P-diffractometer in transmission mode fitted with a location-sensitive detector ☐(OED) and a Cu-anode as X-ray source (CuKα1 radiation, ☐λ=1.54056 Å, 40 kV, 40 mA).

TABLE 4 highest characteristic X-ray powder diffraction peaks for co-crystals obtained from Example 11 and the respective co-crystal former (ccf)

| used ccf | ratio Example 11: ccf | 4 highest characteristic x-ray powder diffraction peaks 2-theta [°] | | | |
|---|---|---|---|---|---|
| ascorbic acid | 1:0.5 | 10.75 | 16.04 | 17.26 | 19.41 |
| mucic acid | 1:0.5-2 | 10.73 | 16.14 | 19.61 | 30.71 |
| pamoic acid | 1:1.25 | 9.45 | 15.63 | 26.27 | 29.90 |
| succinamide | 1:1-2 | 16.16 | 18.39 | 19.83 | 22.24 |
| nicotinic acid | 1:1.1-1.2 | 6.29 | 14.64 | 18.71 | 26.66 |
| nicotinamide | 1:1-1.1 | 14.68 | 18.58 | 24.11 | 26.51 |
| isonicotinamide | 1:1-1.1 | 13.30 | 14.70 | 17.46 | 18.60 |
| hydrated l-lysine | 1:0.8-1 | 11.32 | 14.69 | 18.61 | 21.99 |
| hydrated l-lysine* | 1:0.8-1 | 13.30* | 23.98* | 24.62* | 31.45* |
| l-proline | 1:1.1 | 16.39 | 17.69 | 18.71 | 21.55 |

*hydrated l-lysine co-crystal obtained after dynamical vapour sorption -experiment of l-lysine co-crystal (exposure of rel. humidity in the range of 10-90%)

TABLE 4 highest characteristic X-ray powder diffraction peaks for salts of example 11 (#Methyl-isobutyl-ketone)

| salt | 4 highest characteristic x-ray powder diffraction peaks 2-theta [°] | | | |
|---|---|---|---|---|
| (S)-(S)-(+)-2,3-dibenzoyl-tartrate | 3.72 | 13.60 | 16.89 | 19.34 |
| dihydrochloride | 16.02 | 16.86 | 19.45 | 19.71 |
| dihydrochloride*1.5H$_2$O | 5.10 | 10.67 | 16.07 | 25.13 |
| dihydrochloride*MIBK# | 5.08 | 15.97 | 16.81 | 18.56 |

Pharmacological Part

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The CCR3 receptor binding test is based on a K562 cell line (leukemia myelogenic blast cells) transfected with the human chemokine receptor CCR3 (hCCR3-C1 cells). The cell membranes were prepared by disrupting the hCCR3-C1 cells by nitrogen decomposition. The preparation was centrifuged at 400 g 4° C. for 30 min. The supernatant was transferred into fresh tubes followed by a second centrifugation at 48000 g, 4° C. for 1 h. The membranes were re-suspended in the SPA incubation buffer (25 mM HEPES, 25 mM MgCl$_2$ 6×H$_2$O, 1 mM CaCl$_2$ 2×H$_2$O) without bovine serum albumin and homogenized by passing through a single use needle (Terumo, 23Gx1"). The membranes were stored in aliquots at −80° C.

The CCR3 receptor binding assay was performed in a Scintillation Proximity Assay (SPA) design with the radioligand recombinant human $^{125}$Iodine-eotaxin-1. Cell membranes of hCCR3C1 cells were again homogenized by passing through a single use needle (Terumo, 23Gx1") and diluted in SPA incubation buffer in suitable concentrations (0.5-10 µg protein/well) in 96 well microtiter plates (1450-514, Perkin Elmer). The SPA assay was set up in the SPA incubation buffer with a final volume of 200 µl and final concentration of 25 mM HEPES, 25 mM MgCl$_2$ 6×H$_2$O, 1 mM CaCl$_2$ 2×H$_2$O and 0.1% bovine serum albumin. The SPA assay mixture contained 60 µl of the membrane suspension, 80 µl of Wheat Germ Agglutinin coated PVT beads (organic scintillator, GE Healthcare, RPNQ-0001) 0.2 mg/well), 40 µl of recombinant human $^{125}$Jodine-eotaxin-1 (Biotrend), diluted in SPA buffer to a final concentration of 30.000 dpm per well, and 20 µl of the test compound (dissolved in DMSO dilutions). The SPA assay mixture was incubated for 2 h at room temperature. Bound radioactivity was determined with a scintillation counter (Micro Beta "Trilux", Wallac). Included were controls for total binding (no displacer added, Bo) and non-specific binding (NSB) by adding unlabelled recombinant human Eotaxin-1 (Biotrend, Cat #300-21) or a reference compound.

Determination of the affinity of a test compound was calculated by subtraction of the non-specific binding (NSB) from the total binding (Bo) or the binding in the presence of the test compound (B) at a given compound concentration. The NSB value was set to 100% inhibition. The Bo-NSB value was set to 0% inhibition.

The dissociation constant $K_i$ was calculated by iterative fitting of experimental data obtained at several compound concentrations over a dose range from 0.1 to 10000 nM using the law of mass action based program "easy sys" (Schittkowski, Num Math 68, 129-142 (1994)).

The utility of the compounds in accordance with the present invention as inhibitors of chemokine receptor activity may be demonstrated by methodology known in the art, such as the assays for CCR3 ligand binding, as disclosed by Ponath et al., J. Exp. Med., 183, 2437-2448 (1996) and Uguccioni et al., J. Clin. Invest., 100, 11371143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as L1.2, K562, CHO or HEK-293 cells. Finally, blood or tissue cells, for example human peripheral blood eosinophils, isolated using methods as described by Hansel et al., J. Immunol. Methods, 145, 105-110 (1991), can be utilized in such assays. In particular, the compounds of the present invention have activity in binding to the CCR3 receptor in the aforementioned assays and inhibit the activation of CCR3 by CCR3 ligands, including eotaxin-1, eotaxin-2, eotaxin-3, MCP-2, MCP-3, MCP-4 or RANTES.

As used herein, "activity" is intended to mean a compound demonstrating an inhibition of 50% at 1 µM or higher in inhibition when measured in the aforementioned assays. Such a result is indicative of the intrinsic activity of the compounds as inhibitor of CCR3 receptor activity.

Ki values are (human Eotaxin-1 at human CCR3-Rezeptor):

| # | hCCR3 Ki (nM) |
|---|---|
| 1 | 23.4 |
| 2 | 69.6 |
| 3 | 46.5 |
| 4 | 67.5 |
| 5 | 196.6 |
| 6 | 72.0 |
| 7 | 10.4 |
| 8 | 8.5 |
| 9 | 0.9 |
| 10 | 6.0 |
| 11 | 3.2 |
| 12 | 4.7 |
| 13 | 19.1 |
| 14 | 1401.6 |
| 15 | 3.5 |
| 16 | 6.8 |
| 17 | 4.3 |
| 18 | 4.6 |
| 19 | 4.0 |
| 21 | 5.2 |
| 22 | 2.3 |
| 23 | 4.2 |
| 24 | 5.8 |
| 25 | 8.3 |
| 26 | 231.6 |
| 27 | 413.8 |
| 28 | 17.8 |
| 29 | 4.1 |
| 30 | 70.3 |
| 31 | 87.2 |
| 32 | 2.3 |
| 33 | 7.9 |
| 34 | 7.9 |
| 35 | 61.3 |
| 36 | 1.7 |

Indications

The co-crystals and salts of the compounds of formula 1 as described above are useful for manufacturing a medicament for the prevention and/or treatment of diseases wherein the activity of a CCR3-receptor is involved.

Preferred is the manufacturing of a medicament for the prevention and/or treatment of a wide variety of inflammatory, infectious, and immunoregulatory disorders and diseases of the respiratory or gastrointestinal complaints, inflammatory diseases of the joints and allergic diseases of the nasopharynx, eyes, and skin, including asthma and allergic diseases, eosinophilic diseases, infection by pathogenic microbes (which, by definition, includes viruses), as well as autoimmune pathologies such as the rheumatoid arthritis and atherosclerosis, as well as diseases associated with abnormal enhanced neovascularization such as age-related macular degeneration (AMD), diabetic retinopathy and diabetic macular edema Age-related macular degeneration is a leading cause of blindness world wide. Most blindness in AMD results from invasion of the retina by choroidal neovascularization. CCR3 is specifically expressed in choroidal neovascular endothelial cells of AMD patients. In an often used mouse animal model for AMD laser injury-induced choroidal neovascularization was diminished by genetic depletion of CCR3 or CCR3 ligands as well as by treatment of the mice with an anti-CCR3 antibody or an CCR3 antagonist (Takeda et al, Nature 2009, 460(7252):225-30)

Most preferred is the manufacturing of a medicament for the prevention and/or treatment of e.g. inflammatory or allergic diseases and conditions, including respiratory allergic diseases such as asthma, perennial and seasonal allergic rhinitis, allergic conjunctivitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); non-allergic asthma; Exercise induced bronchoconstriction; systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, immune thrombocytopenia (adult ITP, neonatal thrombocytopenia, paediatric ITP), immune haemolytic anaemia (auto-immune and drug induced), Evans syndrome (platelet and red cell immune cytopaenias), Rh disease of the newborn, Goodpasture's syndrome (anti-GBM disease), Celiac, Auto-immune cardio-myopathy juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); erythema nodosum; eosinophilic myositis, eosinophilic fasciitis; cancers with leukocyte infiltration of the skin or organs; chronic obstructive pulmonary disease, age-related macular degeneration (AMD), diabetic retinopathy and diabetic macular edema.

Method of Treatment

Accordingly, the present invention is directed to co-crystals and salts of compounds of formula 1 as described above which are useful in the prevention and/or treatment of a wide variety of inflammatory, infectious, and immunoregulatory disorders and diseases, including asthma and allergic diseases, chronic obstructive pulmonary disease, infection by pathogenic microbes (which, by definition, includes viruses), autoimmune pathologies such as the rheumatoid arthritis and atherosclerosis as well as age-related macular degeneration (AMD), diabetic retinopathy and diabetic macular edema.

For example a co-crystal or salt of an instant compound which inhibits one or more functions of a mammalian chemokine receptor (e.g., a human chemokine receptor) may be administered to inhibit (i.e., reduce or prevent) inflammation, infectious diseases or abnormal enhanced neovascularization. As a result, one or more inflammatory process, such as leukocyte emigration, adhesion, chemotaxis, exocytosis (e.g., of enzymes, growth factors, histamine) or inflammatory mediator release, survival or proliferation of CCR3 expressing cells is inhibited. For example, eosinophilic infiltration to inflammatory sites (e.g., in asthma or allergic rhinitis) can be inhibited according to the present method. In particular, the co-crystal or salt of the following examples has activity in blocking the activation and migration of cells expressing the CCR3 receptor using the appropriate chemokines in the aforementioned assays. In another instance, endothelial proliferation and neovascularization may be inhibited (i.e., reduced or prevented). As a result abnormal enhanced neovascularization, i.e. of the retina, is inhibited.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom inhibition of chemokine receptor activity is desired.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); chronic obstructive pulmonary disease (including rhinovirus-induced exacerbations); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Also diseases associated with abnormal enhanced neovascularization such as age-related macular degeneration (AMD), diabetic retinopathy and diabetic macular edema can be treated.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combinations

The co-crystals and salts of compounds of formula 1 as described above may be used on their own or combined with other active substances of formula 1 according to the invention. The compounds of general formula 1 may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κβ signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Non-steroidale anti-inflammatory agents (NSAIDs), CRTH2 antagonists, DP1-receptor modulators, Thromboxane receptor antagonists, CCR3 antagonists, $CCR^4$ antagonists, $CCR^1$ antagonists, CCR5 antagonists, CCR6 antagonists, CCR7 antagonists, CCR8 antagonists, CCR9 antagonists, CCR30 antagonists, $CXCR^3$ antagonists, $CXCR^4$ antagonists, $CXCR^2$ antagonists, $CXCR^1$ antagonists, CXCR5 antagonists, CXCR6 antagonists, $CX3CR^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, but also combinations of two or three active substances, i.e.:

Betamimetics with corticosteroids, PDE4-inhibitors, CRTH2-inhibitors or LTD4-antagonists, Anticholinergics with betamimetics, corticosteroids, PDE4-inhibitors, CRTH2-inhibitors or LTD4-antagonists, Corticosteroids with PDE4-inhibitors, CRTH2-inhibitors or LTD4-antagonists PDE4-inhibitors with CRTH2-inhibitors or LTD4-antagonists CRTH2-inhibitors with LTD4-antagonists.

Pharmaceutical Forms

Suitable preparations for administering the co-crystals or salts of compounds of formula 1 include for example tablets, capsules, suppositories, solutions and powders etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

For administering the co-crystals or salts of compounds of formula 1 it is particularly preferred according to the invention to use preparations or pharmaceutical formulations which are suitable for inhalation. Inhalable preparations include inhalable powders, propellant-containing metered-dose aerosols or propellant-free inhalable solutions. Within the scope of the present invention, the term propellant-free inhalable solutions also include concentrates or sterile inhalable solutions ready for use. The formulations which may be used within the scope of the present invention are described in more detail in the next part of the specification.

The inhalable powders which may be used according to the invention may contain a co-crystal or salt of 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipient mentioned above. These finer excipients are also selected from the group of possible excipients listed hereinbefore. Finally, in order to prepare the inhalable powders according to the invention, micronized active substance 1, preferably with an average particle size of 0.5 to 10 μm, more preferably from 1 to 5 μm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain a co-crystal or and salt of 1 dissolved in the propellant gas or in dispersed form. The co-crystals or salts of 1 may be contained in separate formulations or in a common formulation, in which the co-crystals or salts of 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing a co-crystal or salt of 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances.

Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred. Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the co-crystal or salt of 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the μg range. The co-crystals or salts of compounds of formula 1 may also be used effectively above the μg range. The dosage may then be in the gram range, for example.

In another aspect the present invention relates to the abovementioned pharmaceutical formulations as such which are characterised in that they contain a co-crystal or salt of a compound of formula 1, particularly the above-mentioned pharmaceutical formulations which can be administered by inhalation.

The following examples of formulations illustrate the present invention without restricting its scope:

Examples of Pharmaceutical Formulations

| A) | Tablets | per tablet |
|---|---|---|
| | active substance 1 | 100 mg |
| | lactose | 140 mg |
| | maize starch | 240 mg |
| | polyvinylpyrrolidone | 15 mg |
| | magnesium stearate | 5 mg |
| | | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) | Tablets | per tablet |
|---|---|---|
| | active substance 1 | 80 mg |
| | lactose | 55 mg |
| | maize starch | 190 mg |
| | microcrystalline cellulose | 35 mg |
| | polyvinylpyrrolidone | 15 mg |
| | sodium carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance 1 | 50 mg |
| | sodium chloride | 50 mg |
| | water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

| D) | Metering aerosol | |
|---|---|---|
| | active substance 1 | 0.005 |
| | sorbitan trioleate | 0.1 |

| D) | Metering aerosol | |
|---|---|---|
| | monofluorotrichloromethane and TG134a:TG227 2:1 | ad 100 |

The suspension is transferred into a conventional aerosol container with metering valve. Preferably 50 µl suspension are released on each actuation. The active substance may also be released in higher doses if desired (e.g. 0.02 wt.-%).

| E) | Solutions (in mg/100 ml) | |
|---|---|---|
| | active substance 1 | 333.3 mg |
| | benzalkonium chloride | 10.0 mg |
| | EDTA | 50.0 mg |
| | HCl (1N) | ad pH 2.4 |

This solution can be prepared in the usual way.

| F) | Inhalable powder | |
|---|---|---|
| | active substance 1 | 12 µg |
| | lactose monohydrate | ad 25 mg |

The inhalable powder is prepared in the usual way by mixing the individual ingredients.

What we claim:

1. A crystalline salt of formula 1a

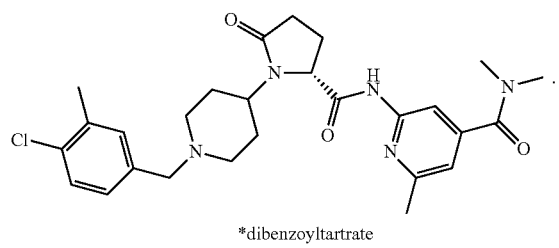

*dibenzoyltartrate

2. A crystalline salt of formula 1b

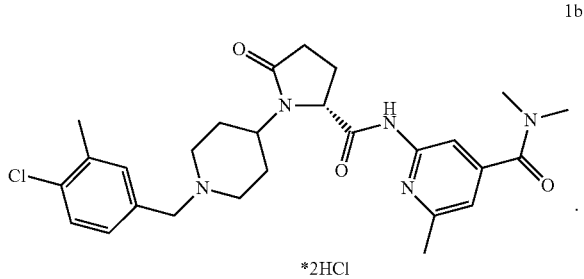 [SMILES: Cc1cc(C(=O)N(C)C)cc(NC(=O)[C@H]2CCC(=O)N2C2CCN(Cc3ccc(Cl)c(C)c3)CC2)n1]

*2HCl

3. The crystalline salt according to claim 1 characterized in that the four highest X-ray powder diffraction peaks occur at 3.72, 13.60, 16.89 and 19.34 degrees 2θ (±0.05 degrees 2θ) when measured using CuKα radiation.

4. The crystalline salt according to claim 2 characterized in that the four highest X-ray powder diffraction peaks occur at 16.02, 16.86, 19.45 and 19.71 degrees 2θ (±0.05 degrees 2θ) when measured using CuKα radiation.

* * * * *